(12) United States Patent
Hamauzu

(10) Patent No.: US 11,801,019 B2
(45) Date of Patent: *Oct. 31, 2023

(54) POSITIONAL INFORMATION DISPLAY DEVICE, POSITIONAL INFORMATION DISPLAY METHOD, POSITIONAL INFORMATION DISPLAY PROGRAM, AND RADIOGRAPHY APPARATUS

(71) Applicant: FUJIFILM Corporation, Tokyo (JP)

(72) Inventor: Shin Hamauzu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 113 days.

This patent is subject to a terminal disclaimer.

(21) Appl. No.: 16/813,693

(22) Filed: Mar. 9, 2020

(65) Prior Publication Data

US 2020/0305831 A1 Oct. 1, 2020

(30) Foreign Application Priority Data

Mar. 27, 2019 (JP) ................................. 2019-060369

(51) Int. Cl.
*A61B 6/00* (2006.01)
*A61B 6/03* (2006.01)
(Continued)

(52) U.S. Cl.
CPC ................ *A61B 6/12* (2013.01); *A61B 6/032* (2013.01); *A61B 6/0492* (2013.01);
(Continued)

(58) Field of Classification Search
CPC ........... A61B 6/04; A61B 6/0492; A61B 6/08; A61B 6/42; A61B 6/46; A61B 6/461;
(Continued)

(56) References Cited

U.S. PATENT DOCUMENTS 6,027,510 A * 2/2000 Alt ......................... A61F 2/958
606/108
6,222,906 B1 * 4/2001 Sakaguchi ........ H01L 27/14663
378/95

(Continued)

FOREIGN PATENT DOCUMENTS

JP 2000070259 3/2000
JP 2009034494 2/2009
(Continued)

OTHER PUBLICATIONS

An English Translation of JP2014102746A by Patent Translate. (Year: 2023).*

(Continued)

*Primary Examiner* — Allen C. Ho
(74) *Attorney, Agent, or Firm* — JCIPRNET

(57) ABSTRACT

A first positional information derivation unit derives three-dimensional positional information of at least one target point of a target structure in a subject as first positional information. A second positional information derivation unit derives three-dimensional positional information of at least one feature point on an insertion structure inserted to the target structure in the subject as second positional information. A display control unit displays a positional information screen indicating a positional relationship between the target point and the feature point on a display unit.

22 Claims, 10 Drawing Sheets

(51) Int. Cl.
- *A61B 6/12* (2006.01)
- *A61B 6/04* (2006.01)
- *A61B 17/16* (2006.01)
- *A61F 2/95* (2013.01)
- *A61B 17/17* (2006.01)

(52) U.S. Cl.
CPC .......... *A61B 6/4007* (2013.01); *A61B 6/4225* (2013.01); *A61B 6/4405* (2013.01); *A61B 6/4441* (2013.01); *A61B 6/463* (2013.01); *A61B 6/466* (2013.01); *A61B 6/467* (2013.01); *A61B 6/486* (2013.01); *A61B 6/487* (2013.01); *A61B 6/503* (2013.01); *A61B 6/504* (2013.01); *A61B 6/505* (2013.01); *A61B 6/5205* (2013.01); *A61B 6/5211* (2013.01); *A61B 6/5294* (2013.01); *A61B 6/54* (2013.01); *A61B 17/1626* (2013.01); *A61B 17/1703* (2013.01); *A61F 2/95* (2013.01)

(58) Field of Classification Search
CPC ... A61B 6/463–467; A61B 6/486; A61B 6/52; A61B 6/5211; A61B 6/5294; A61B 6/547; A61B 17/16; A61B 17/1613; A61B 17/17; A61B 17/1703; A61B 17/1728; A61B 17/1739; A61B 17/1757; A61B 34/10; A61B 34/20; A61B 34/25; A61B 34/30; A61B 34/70; A61B 90/37; A61B 90/39; A61B 2034/107; A61B 2034/2046; A61B 2034/2065; A61B 2034/301–303; A61B 2090/363–365; A61B 2090/376; A61B 2090/3966; A61B 2090/3983; A61B 2576/02; A61B 2576/023; A61B 2034/302; A61B 2090/364; A61B 6/464; A61B 6/465; A61B 6/466; A61B 6/032; A61B 6/035; A61B 6/12; A61B 6/40; A61B 6/4007; A61B 6/4208; A61B 6/4233; A61B 6/4283; A61B 6/44; A61B 6/4405; A61B 6/4429; A61B 6/4435; A61B 6/4441; A61B 6/4447; A61B 6/469; A61B 6/487; A61B 6/503; A61B 6/504; A61B 6/5205; A61B 6/54; A61B 6/542; A61B 6/545; A61B 6/588; A61B 6/4225; A61B 6/505; A61B 6/5217; A61B 2034/303; A61B 2090/365; A61F 2/95; G06T 7/0012; G06T 7/0014; G06T 7/0016; G06T 7/30; G06T 7/33; G06T 7/38; G06T 7/60; G06T 7/66; G06T 7/70; G06T 7/73; G06T 7/97; G06T 2210/41; G06T 2207/10116; G06T 2207/10121; G06T 2207/20; G06T 2207/20092; G06T 2207/20101; G06T 2207/20104; G06T 2207/30; G06T 2207/30004; G06T 2207/30008; G06T 2207/30012; G06T 2207/30021; G06T 2207/30048; G06T 2207/30101; G06T 2207/30104; G06T 2211/40; G06T 2211/404
USPC ........ 378/9, 62, 98.5, 196–198, 207, 41, 42; 382/130–132; 600/424, 425
See application file for complete search history.

(56) References Cited

U.S. PATENT DOCUMENTS

| | | | | |
|---|---|---|---|---|
| 7,649,973 B1* | 1/2010 | Li | ................... | A61B 6/032 378/16 |
| 7,809,102 B2* | 10/2010 | Brada | ................... | A61B 6/463 378/20 |
| 7,826,585 B2* | 11/2010 | Proksa | ................... | G01T 1/1647 378/5 |
| 7,869,561 B2* | 1/2011 | Dafni | ................... | H05G 1/70 378/19 |
| 7,933,378 B2* | 4/2011 | Proksa | ................... | A61B 6/4014 378/9 |
| 7,949,089 B2* | 5/2011 | Dafni | ................... | A61B 6/481 378/9 |
| 7,991,114 B2* | 8/2011 | Okunuki | ................... | A61B 6/032 378/197 |
| 8,180,017 B2* | 5/2012 | Forthmann | ................... | H01J 35/10 378/156 |
| 8,270,562 B2* | 9/2012 | Sainath | ................... | G01T 1/2985 378/124 |
| 8,396,533 B2 | 3/2013 | Barbu et al. | | |
| 8,693,638 B2* | 4/2014 | Dafni | ................... | H01J 35/153 378/124 |
| 8,699,657 B2* | 4/2014 | Baeumer | ................... | A61B 6/482 378/92 |
| 8,768,030 B2* | 7/2014 | Bruder | ................... | A61B 6/482 378/92 |
| 8,908,826 B2* | 12/2014 | Bernhardt | ................... | A61B 6/50 378/42 |
| 8,964,942 B2* | 2/2015 | Dafni | ................... | G01T 1/2985 378/150 |
| 8,995,731 B2* | 3/2015 | Joglekar | ................... | A61B 6/12 382/128 |
| 9,510,771 B1 | 12/2016 | Finley et al. | | |
| 9,579,071 B2* | 2/2017 | Lee | ................... | A61B 6/022 |
| 9,801,602 B2* | 10/2017 | Nagae | ................... | A61B 6/504 |
| 9,833,210 B2* | 12/2017 | Sakaguchi | ................... | A61B 6/5264 |
| 10,154,239 B2* | 12/2018 | Casas | ................... | G06F 3/011 |
| 10,278,667 B2* | 5/2019 | Iijima | ................... | A61B 6/5258 |
| 10,478,143 B2* | 11/2019 | Merlet | ................... | A61B 6/487 |
| 10,825,257 B2* | 11/2020 | Auvray | ................... | G06T 11/008 |
| 10,856,825 B2* | 12/2020 | Dargis | ................... | G06T 11/005 |
| 10,893,840 B2* | 1/2021 | Imagawa | ................... | A61B 6/4411 |
| 10,893,842 B2* | 1/2021 | Barak | ................... | A61B 34/20 |
| 10,918,343 B2* | 2/2021 | Fournie | ................... | H04N 5/23264 |
| 10,959,780 B2* | 3/2021 | Dumenil | ................... | A61B 6/504 |
| 11,170,541 B2* | 11/2021 | Morita | ................... | G06T 11/008 |
| 11,224,391 B2* | 1/2022 | Matsuura | ................... | A61B 6/467 |
| 11,436,697 B2* | 9/2022 | Hamauzu | ................... | A61B 6/463 |
| 11,515,031 B2* | 11/2022 | Takaya | ................... | G06T 7/73 |
| 11,627,924 B2* | 4/2023 | Alexandroni | ................... | A61B 6/466 378/1 |
| 11,642,170 B2* | 5/2023 | Blau | ................... | A61B 17/1725 600/424 |
| 2006/0036162 A1* | 2/2006 | Shahidi | ................... | A61B 34/20 600/424 |
| 2007/0225553 A1* | 9/2007 | Shahidi | ................... | A61B 8/12 600/103 |
| 2009/0257551 A1* | 10/2009 | Dafni | ................... | A61B 6/4014 378/9 |
| 2016/0199147 A1* | 7/2016 | Shin | ................... | A61B 90/36 600/411 |
| 2018/0262743 A1* | 9/2018 | Casas | ................... | G06F 3/04845 |
| 2020/0305826 A1* | 10/2020 | Hamauzu | ................... | A61B 6/022 |

FOREIGN PATENT DOCUMENTS

| | | | |
|---|---|---|---|
| JP | 2009066396 | 4/2009 | |
| JP | 2013066802 | 4/2013 | |
| JP | 2014102746 | 6/2014 | |
| JP | 2017185007 | 10/2017 | |
| WO | WO-2018132804 A1 * | 7/2018 | ............... A61B 5/05 |

OTHER PUBLICATIONS

"Office Action of Japan Counterpart Application" with English translation thereof, dated Jan. 18, 2022, p. 1-p. 6.

Office Action of Japan Counterpart Application, with English translation thereof, dated Jul. 26, 2022, pp. 1-6.

Office Action of Japan Counterpart Application, with English translation thereof, dated Jan. 17, 2023, pp. 1-5.

(56) References Cited

OTHER PUBLICATIONS

"Decision of Refusal of Japan Counterpart Application", dated Jun. 13, 2023, with English translation thereof, p. 1-p. 3.

* cited by examiner

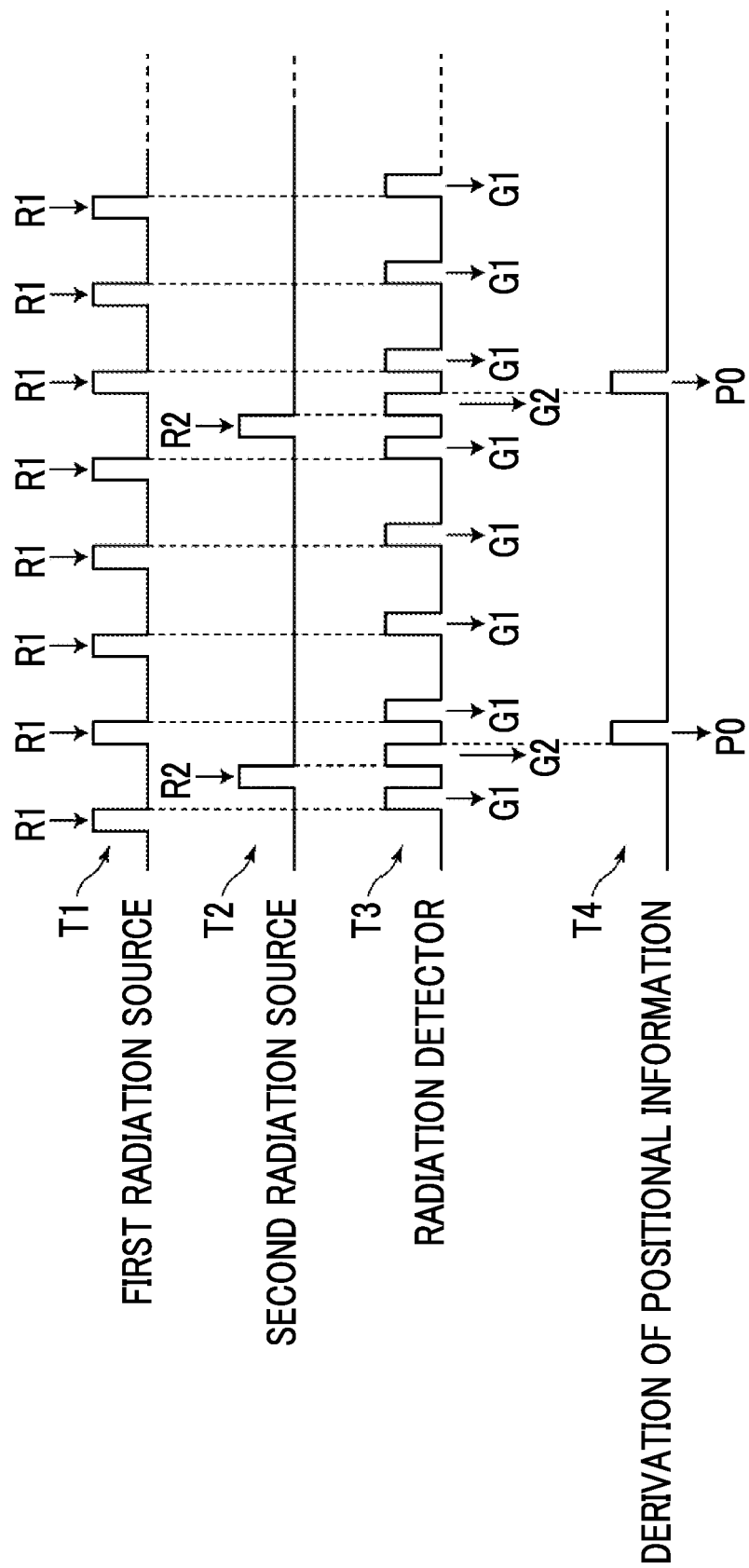

POSITIONAL INFORMATION DISPLAY DEVICE, POSITIONAL INFORMATION DISPLAY METHOD, POSITIONAL INFORMATION DISPLAY PROGRAM, AND RADIOGRAPHY APPARATUS

CROSS REFERENCE TO RELATED APPLICATIONS

The present application claims priority under 35 U.S.C. § 119 to Japanese Patent Application No. 2019-060369 filed on Mar. 27, 2019. The above application is hereby expressly incorporated by reference, in its entirety, into the present application.

BACKGROUND

Technical Filed

The present disclosure relates to a positional information display device, a positional information display method, a positional information display program, and a radiography apparatus.

Related Art

In surgical operations and catheter treatments, it is necessary to understand the positional relationship between surgical instruments and human body structures such as bones and blood vessels. However, in the related art, in many cases, the understanding of the positional relationship between a surgical instrument and a human body structure depends on the experience and intuition of a doctor and there are problems of an error in the insertion of the surgical instrument and excessive surgery time. For this reason, a process is performed which captures an image of a subject using a radioscopy apparatus during surgery and understands the positional relationship between a surgical instrument and a human body structure using a radioscopic image displayed on a display by imaging. However, while a three-dimensional positional relationship is established between the surgical instrument and the human body structure, the radioscopic image is a two-dimensional image. It is difficult for the user to understand the three-dimensional positional relationship between the surgical instrument and the human body structure even in a case in which the user views the two-dimensional radioscopic image.

For this reason, a process is performed which understands a three-dimensional positional relationship between a surgical instrument and a human body structure, using radioscopic images in a plurality of directions acquired by capturing the images of a patient as a subject while changing an angle during a medical procedure or by using a plurality of imaging apparatuses at the same time. In addition, a method has been proposed in which a sensor is attached to a surgical instrument to understand the three-dimensional position of the surgical instrument.

However, in a case in which an image of a subject is captured while the angle is changed, it is necessary to move the imaging apparatus during a medical procedure. In addition, in a case in which a plurality of imaging apparatuses are used at the same time, it is not necessary to move the imaging apparatuses, but a work space for the doctor during surgery is reduced, which may hinder the procedure. Further, in the method using a sensor, it is necessary to prepare a sensor.

For this reason, a method has been proposed which aligns a three-dimensional image that is formed by a plurality of tomographic images acquired in advance by, for example, a computed tomography (CT) apparatus and a magnetic resonance imaging (MRI) apparatus and a two-dimensional radiographic image obtained by capturing an image of a leading end of a catheter to synchronize the radiographic image with the tomographic image including the position of the leading end of the catheter in the three-dimensional image and updates and displays the images (see JP2013-066802A). According to the method described in JP2013-066802A, the doctor can check the position of the leading end of the catheter in the subject by viewing the tomographic image. Therefore, it is possible to easily perform a medical procedure.

In surgical operations and catheter treatments, it is necessary to understand the positional relationship between a surgical instrument and a human body structure in real time. However, in the method described in JP2013-066802A, the processing time for aligning the three-dimensional image and the radiographic image is required. In recent years, since the resolution and density resolution of radiographic images have improved, the amount of image data indicating a three-dimensional image and a radiographic image has become very large. Time is required for a process to align the three-dimensional image and the radiographic image having a large amount of data. For this reason, in the method described in JP2013-066802A, it is difficult to understand the position between the surgical instrument and the human body structure in the subject and the positional relationship therebetween in real time.

SUMMARY OF THE INVENTION

The present disclosure has been made in view of the above-mentioned problems and an object of the present disclosure is to provide a technique that enables a user to understand a positional relationship between a structure inserted into a subject, such as a surgical instrument, and a target structure in the subject in real time.

According to the present disclosure, there is provided a positional information display device comprising: a first positional information derivation unit that derives three-dimensional positional information of at least one target point of a target structure in a subject as first positional information; a second positional information derivation unit that derives three-dimensional positional information of at least one feature point on an insertion structure inserted to the target structure in the subject as second positional information; and a display control unit that displays a positional information screen indicating a positional relationship between the target point and the feature point on a display unit.

The positional information display device according to the present disclosure may further comprise: an image acquisition unit that acquires a radiographic image set including a plurality of radiographic images, which have been generated by alternately irradiating the subject with radiation emitted from a plurality of radiation sources provided at different positions and alternately detecting the radiation transmitted through the subject using one detection unit, at a predetermined time interval; and a feature point detection unit that detects the feature point on the insertion structure in the subject from each of the plurality of radiographic images included in the radiographic image set. The second positional information derivation unit may derive the second positional information using a positional relationship between a position of the feature point detected from each of the plurality of radiographic images on a detection surface of the detection unit and positions of the plurality of radiation sources.

The "predetermined time interval" means, for example, a time interval corresponding to the frame rate of a moving image. The predetermined time interval may be, for example, 25 to 60 fps. As a result, in the present disclosure, a combination of radiographic images, such as a moving image, is acquired. In addition, all of the plurality of radiographic images may be acquired at the same time interval or the plurality of radiographic images may be acquired at different time intervals.

In the positional information display device according to the present disclosure, the display control unit may display the positional information screen including a radiographic image display region in which some of the plurality of radiographic images are displayed and a positional relationship display region in which the positional relationship is displayed on the display unit.

The term "some of the radiographic images" means radiographic images acquired on the basis of the transition of radiation emitted from one of the plurality of radiation sources.

The positional information display device according to the present disclosure may further comprise a notification unit that notifies that the feature point has reached the target point.

In the positional information display device according to the present disclosure, the notification unit may issue a warning in a case in which the feature point deviates from the target point by a predetermined distance or angle.

In the positional information display device according to the present disclosure, the insertion structure may be a surgical instrument that is inserted into the subject.

In the positional information display device according to the present disclosure, the target structure may be a stent that is inserted into a blood vessel of the subject. The target point may be a center position of an end portion of the stent. The insertion structure may be a guide wire for expanding the stent. The feature point may be a leading end of the guide wire.

In the positional information display device according to the present disclosure, the target structure may be a lumbar spine of the subject. The target point may be at least one of an insertion position or an arrival position of a screw that is inserted into the lumbar spine. The insertion structure may be the screw. The feature point may be at least one of a leading end or a rear end of the screw.

According to the present disclosure, there is provided a radiography apparatus comprising: a plurality of radiation sources that are provided at a predetermined interval; a detection unit that is provided so as to face the plurality of radiation sources, detects radiation which has been emitted from each of the plurality of radiation sources and transmitted through a subject, and generates a radiographic image of the subject; an imaging control unit that generates a radiographic image set including a plurality of radiographic images at a predetermined time interval by controlling a time point when each of the plurality of radiation sources emits the radiation and a time point when the detection unit detects the radiation transmitted through the subject such that the plurality of radiation sources alternately irradiate the subject with the radiation and the detection unit alternately detects the radiation transmitted through the subject; and the positional information display device according to the present disclosure.

In the radiography apparatus according to the present disclosure, the number of radiation sources may be 2.

In the radiography apparatus according to the present disclosure, the imaging control unit may direct one of the two radiation sources to sequentially emit radiation at a first time interval, direct the other radiation source to sequentially emit radiation at a second time interval equal to or longer than the first time interval, and control the detection unit so as to detect the radiation at all time points when the two radiation sources emit the radiation. The image acquisition unit may acquire, as the radiographic image set, two radiographic images generated by detecting two temporally adjacent radiations which have been emitted from the two radiation sources using the detection unit.

The term "being equal to or longer than the first time interval" means being equal to the first time interval and being longer than the first time interval.

According to the present disclosure, there is provided a positional information display method comprising: deriving three-dimensional positional information of at least one target point of a target structure in a subject as first positional information; deriving three-dimensional positional information of at least one feature point on an insertion structure inserted to the target structure in the subject as second positional information; and displaying a positional information screen indicating a positional relationship between the target point and the feature point on a display unit.

In addition, a program that causes a computer to perform the positional information display method according to the present disclosure may be provided.

According to the present disclosure, there is provided another positional information display device comprising a memory that stores commands to be executed by a computer and a processor that is configured to execute the stored commands. The processor performs a process of deriving three-dimensional positional information of at least one target point of a target structure in a subject as first positional information, a process of deriving three-dimensional positional information of at least one feature point on an insertion structure inserted to the target structure in the subject as second positional information, and a process of displaying a positional information screen indicating a positional relationship between the target point and the feature point on a display unit.

According to the present disclosure, it is possible to understand the positional relationship between the target structure and the insertion structure in the subject in real time.

BRIEF DESCRIPTION OF THE DRAWINGS

FIG. 16 is a diagram illustrating the time point when the first and second radiation sources emit radiation and the time point when the radiation detector detects radiation.

DETAILED DESCRIPTION

Figure 1:
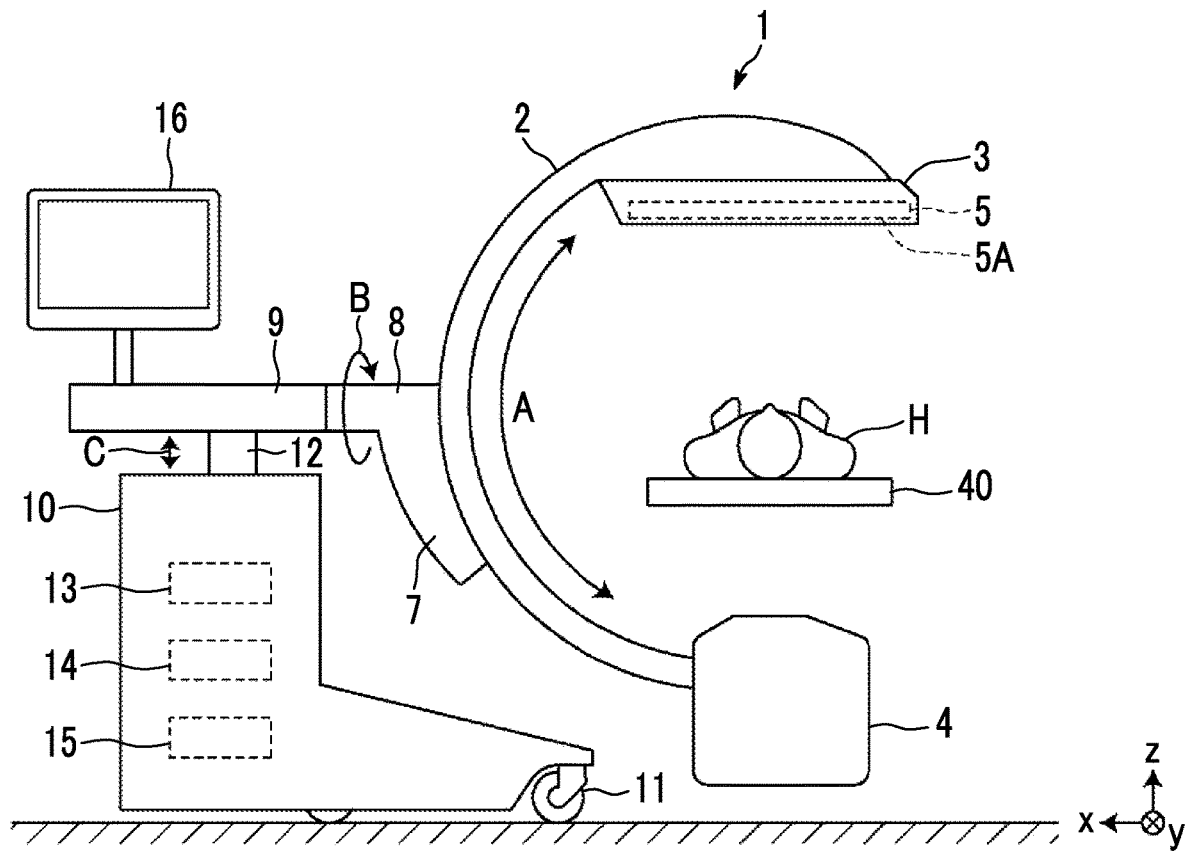
FIG. 1 is a diagram schematically illustrating the configuration of a radiography apparatus to which a positional information display device according to an embodiment of the present disclosure is applied.

Hereinafter, an embodiment of the present disclosure will be described with reference to the drawings. FIG. 1 is a diagram schematically illustrating the configuration of a radiography apparatus to which a positional information display device according to the embodiment of the present disclosure is applied. The radiography apparatus according to this embodiment acquires and displays a radioscopic image of a subject H as a moving image in a case in which, for example, a surgical operation and a catheter treatment are performed on the subject H.

In this embodiment, it is assumed that the x-axis is set as the left-right direction of FIG. 1, the y-axis is set as the depth direction of FIG. 1, and the z-axis is set as a direction perpendicular to the plane on which the radiography apparatus 1 illustrated in FIG. 1 is placed.

As illustrated in FIG. 1, the radiography apparatus 1 according to this embodiment comprises a C-arm 2. An imaging unit 3 is attached to one end portion of the C-arm 2 and a radiation emitting unit 4 is attached to the other end portion so as to face the imaging unit 3.

A radiation detector 5, such as a flat panel detector, is provided in the imaging unit 3. The radiation detector 5 corresponds to a detection unit according to the present disclosure. In addition, for example, a circuit substrate provided with a charge amplifier that converts a charge signal read from the radiation detector 5 into a voltage signal, a correlated double sampling circuit that samples the voltage signal output from the charge amplifier, an analog-to-digital (AD) conversion unit that converts the voltage signal into a digital signal, and the like is provided in the imaging unit 3. In this embodiment, the radiation detector 5 is used. However, the detector is not limited to the radiation detector 5 as long as it can detect radiation and convert the radiation into an image. For example, a detection device, such as an image intensifier, may be used.

The radiation detector 5 can repeatedly perform the recording and reading of a radiographic image and may be a so-called direct-type radiation detector that directly converts radiation, such as X-rays, into charge or a so-called indirect-type radiation detector that converts radiation into visible light and then converts the visible light into a charge signal. In addition, it is preferable that a so-called TFT reading method which turns on and off a thin film transistor (TFT) switch to read a radiographic image signal or a so-called optical reading method which emits reading light to read a radiographic image signal is used as a radiographic image signal reading method. However, the invention is not limited thereto and other reading methods may be used.

Figure 2:
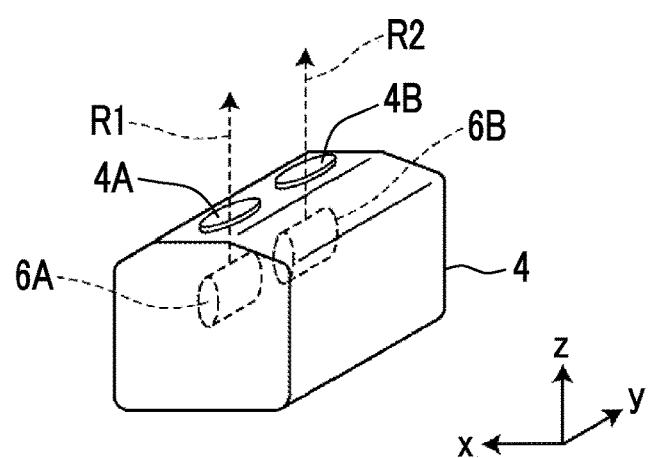
FIG. 2 is a diagram schematically illustrating the configuration of a radiation emitting unit.

FIG. 2 is a diagram schematically illustrating the configuration of the radiation emitting unit 4. As illustrated in FIG. 2, a first radiation source 6A and a second radiation source 6B are provided in the radiation emitting unit 4. The first and second radiation sources 6A and 6B are arranged side by side at a predetermined interval in the depth direction (that is, the y-axis direction) of FIG. 1. First and second radiations R1 and R2 emitted from the first and second radiation sources 6A and 6B are emitted to the imaging unit 3 through first and second emission portions 4A and 4B, respectively.

The first and second radiation sources 6A and 6B emit X-rays as radiation and an imaging control unit 14 which will be described below controls the time point when the first and second radiation sources 6A and 6B emit radiation and the time point when the radiation detector 5 detects the first and second radiations R1 and R2. In addition, for example, the imaging control unit 14 controls the radiation generation conditions of the first and second radiation sources 6A and 6B, that is, the selection of a target and a filter material, a tube voltage, and an irradiation time.

In the radiography apparatus 1 according to this embodiment, a so-called source image distance (SID) which is a distance between a detection surface 5A of the radiation detector 5 and the first and second radiation sources 6A and 6B of the radiation emitting unit 4 is a fixed value.

The C-arm 2 according to this embodiment is held by a C-arm holding portion 7 such that the C-arm 2 can be moved in the direction of an arrow A illustrated in FIG. 1 and the angle of the imaging unit 3 and the radiation emitting unit 4 with respect to the z direction (vertical direction) illustrated in FIG. 1 can be integrally changed. Further, the C-arm holding portion 7 has a shaft portion 8 and the shaft portion 8 connects the C-arm 2 to a bearing 9 so as to be rotatable. Therefore, the C-arm 2 is rotatable on the shaft portion 8 as a rotation axis in the direction of an arrow B illustrated in FIG. 1.

In addition, as illustrated in FIG. 1, the radiography apparatus 1 according to this embodiment comprises a main body unit 10. The main body unit 10 has a plurality of wheels 11 attached to the bottom. Therefore, the radiography apparatus 1 according to this embodiment can be moved. A support shaft 12 that expands and contracts in the z-axis direction of FIG. 1 is provided in an upper part of a housing of the main body unit 10 in FIG. 1. The bearing 9 is held above the support shaft 12 so as to be movable in the direction of an arrow C.

Since the radiography apparatus 1 according to this embodiment has the above-mentioned configuration, the subject H who lies in a supine position on the imaging table 40 is irradiated with radiation from the lower side of the subject H and the radiation detector 5 of the imaging unit 3 detects the radiation transmitted through the subject H to acquire a radiographic image of the subject H. Here, the C-arm 2 is movable in the direction of the arrow A, the direction of the arrow B, and the direction of the arrow C and the radiography apparatus 1 is movable by the wheels 11. Therefore, the radiography apparatus 1 according to this embodiment can capture an image of a desired part of the subject H who lies in a supine position on the imaging table 40 in a desired direction.

The main body unit 10 is provided with an interface (I/F) unit 13, the imaging control unit 14, and a positional information display device 15 according to this embodiment.

The I/F unit 13 has a function of performing wireless or wired communication with an external apparatus and a console that controls the overall operation related to the capture of a radiographic image by the radiography apparatus 1 (which are not illustrated). The radiography apparatus 1 according to this embodiment captures an image of the subject H on the basis of an imaging command received from the console through the I/F unit 13.

The imaging control unit 14 directs the first and second radiation sources 6A and 6B of the radiation emitting unit 4 to emit the first and second radiations R1 and R2 on the basis of the imaging conditions associated with an imaging command from the console, respectively. In addition, the imaging control unit 14 directs the radiation detector 5 of the imaging unit 3 to detect the first and second radiations R1 and R2 transmitted through the subject H according to the time point when the first and second radiations R1 and R2 are emitted from the first and second radiation sources 6A and 6B, respectively, and generates first and second radiographic images G1 and G2 of the subject H. The generated first and second radiographic images G1 and G2 are output to the main body unit 10. The time point when the first and second radiations R1 and R2 are emitted from the first and second radiation sources 6A and 6B, respectively, and the time point when the radiation detector 5 detects the first and second radiations R1 and R2 will be described below.

In addition, a user interface 16 is provided above the main body unit 10. The user interface 16 has a function by which a user, such as a technician or a doctor who takes a radiographic image using the radiography apparatus 1, inputs a command related to the capture of a radiographic image, a function which displays a radiographic image acquired by imaging as a radioscopic image, and a function which provides information related to the capture of a radiographic image to the user. A touch panel display is given an example of the user interface 16.

Figure 3:
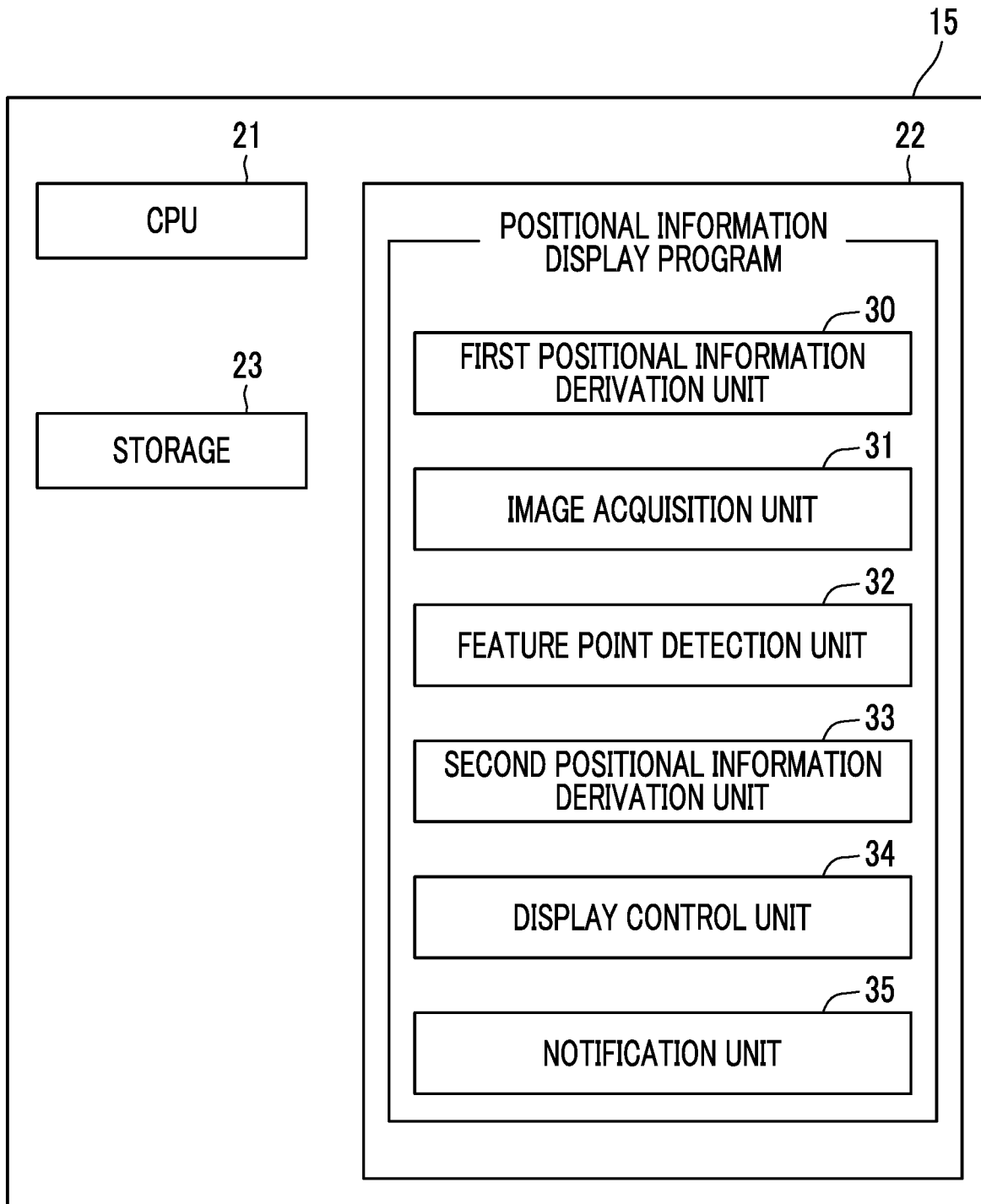
FIG. 3 is a diagram schematically illustrating the configuration of the positional information display device implemented by installing a positional information display program in a computer in this embodiment.

Next, the positional information display device according to this embodiment will be described. FIG. 3 is a diagram schematically illustrating the configuration of the positional information display device according to this embodiment. As illustrated in FIG. 3, the positional information display device 15 is a computer and comprises a central processing unit (CPU) 21, a memory 22, and a storage 23 as the configuration of a standard computer.

A positional information display program according to this embodiment is installed in the positional information display device 15 according to this embodiment. The positional information display program is stored in a storage device of a server computer connected to the network or a network storage such that it can be accessed from the outside, is downloaded to the positional information display device 15 through the I/F unit 13 on demand, and is installed in the positional information display device 15. Alternatively, the positional information display program is recorded on a recording medium, such as a digital versatile disc (DVD) or a compact disc read only memory (CD-ROM), is distributed, and is installed in the positional information display device 15 from the recording medium.

The storage 23 is a storage device, such as a hard disk drive or a solid state drive (SSD), and stores various kinds of information including the positional information display program. The radiographic image acquired by imaging is also stored in the storage 23.

For example, the programs stored in the storage 23 are temporarily stored in the memory 22 in order to cause the CPU 21 to perform various processes. The positional information display program defines, as processes performed by the CPU 21, a first positional information derivation process that derives three-dimensional positional information of at least one target point of a target structure in the subject H as first positional information, an image acquisition process that acquires a radiographic image set including the first and second radiographic images G1 and G2 acquired by the radiography apparatus 1 at a predetermined time interval, a feature point detection process that detects at least one common feature point on an insertion structure inserted into the target structure in the subject H from each of the first and second radiographic images G1 and G2 included in the radiographic image set, a second positional information derivation process that derives three-dimensional positional information of at least one feature point in the subject H as second positional information, using a positional relationship between the position of the feature point detected from the first and second radiographic images G1 and G2 on the detection surface 5A of the radiation detector 5 and the positions of the first and second radiation sources 6A and 6B, a display control process that displays a positional information screen indicating a positional relationship between the target point and the feature point on the user interface 16, and a notification process that notifies that the feature point has reached the target point.

Then, the CPU 21 performs these processes according to the positional information display program such that the computer functions as the positional information display device 15 comprising a first positional information derivation unit 30, an image acquisition unit 31, a feature point detection unit 32, a second positional information derivation unit 33, a display control unit 34, and a notification unit 35.

The first positional information derivation unit 30 derives the three-dimensional positional information of at least one target point of the target structure in the subject H as the first positional information. The first positional information derivation unit 30 will be described below.

Figure 4:
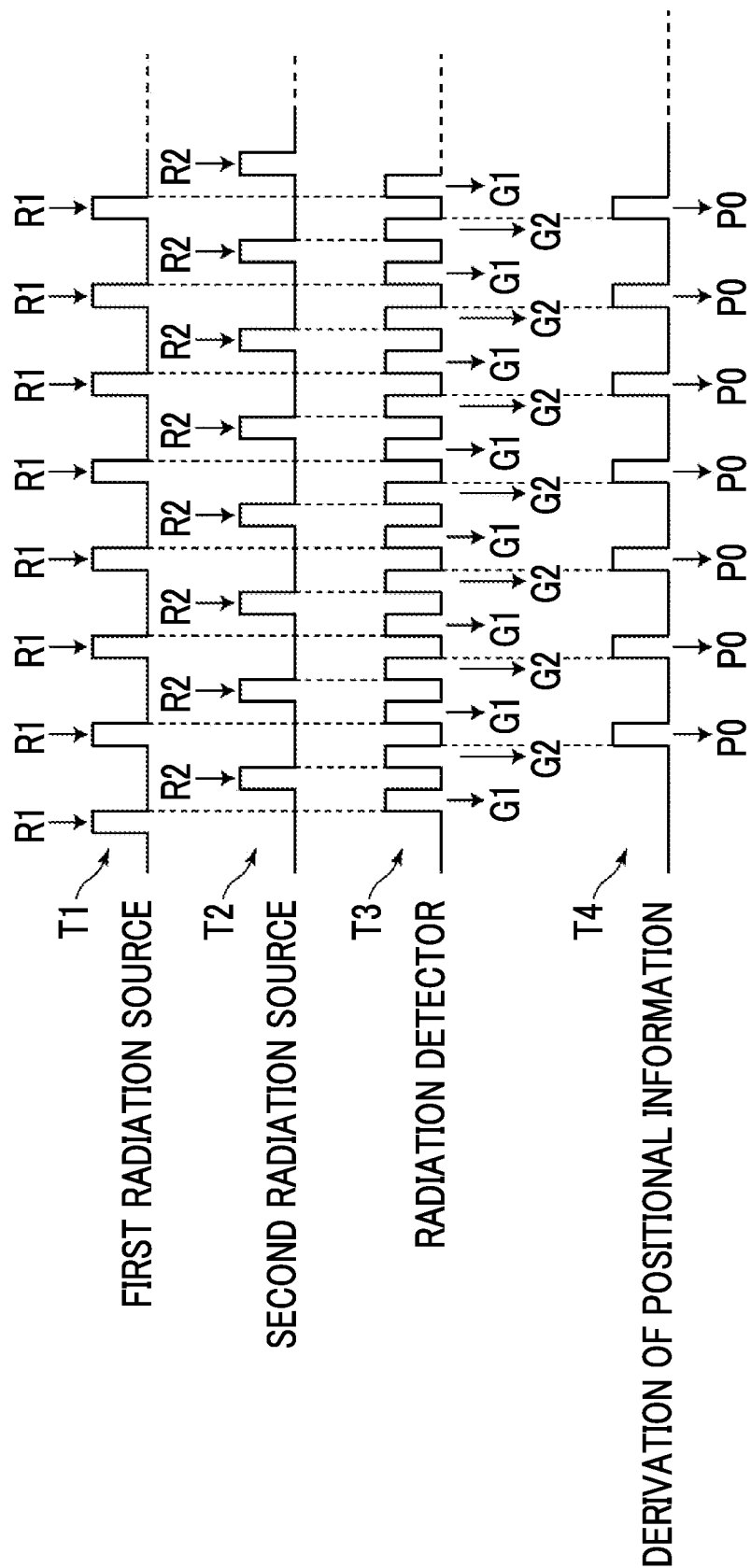
FIG. 4 is a diagram illustrating the time point when first and second radiation sources emit radiation and the time point when a radiation detector detects radiation.

The image acquisition unit 31 acquires a radiographic image set including the first and second radiographic images G1 and G2 of the subject H generated by the control of the imaging control unit 14 for the first and second radiation sources 6A and 6B and the radiation detector 5. Next, the time point when the first and second radiation sources 6A and 6B emit the first and second radiations R1 and R2 and the time point when the radiation detector 5 detects the first and second radiations R1 and R2 will be described. FIG. 4 is a diagram illustrating the time point when the first and second radiation sources 6A and 6B emit the first and second radiations R1 and R2 and the time point when the radiation detector 5 detects the first and second radiations R1 and R2.

FIG. 4 illustrates a time point T1 when the first radiation source 6A emits the first radiation R1, a time point T2 when the second radiation source 6B emits the second radiation R2, and a time point T3 when the radiation detector 5 detects the first and second radiations R1 and R2. In addition, T4 is a second positional information derivation time point which will be described below.

As illustrated in FIG. 4, in a case in which the first radiation R1 is emitted from the first radiation source 6A, the radiation detector 5 detects the first radiation R1 transmitted through the subject H and generates the first radiographic image G1. In a case in which the radiation detector 5 generates the first radiographic image G1, the second radiation source 6B emits the second radiation R2 and the radiation detector 5 detects the second radiation R2 transmitted through the subject H and generates the second radiographic image G2. In a case in which the radiation detector 5 generates the second radiographic image G2, the first radiation source 6A emits the next first radiation R1 and the radiation detector 5 detects the next first radiation R1 transmitted through the subject H and generates the next first radiographic image G1. This is repeated to alternately and repeatedly acquire the first radiographic image G1 and the second radiographic image G2. The image acquisition unit 31 acquires the first and second radiographic images G1 and G2 that are temporally adjacent to each other as the radiographic image set.

The time interval at which the radiation detector 5 generates the first and second radiographic images G1 and G2 is 25 to 60 fps, for example, 30 fps. In a case in which the time interval at which the first and second radiographic images G1 and G2 are generated is 30 fps, the time point when the first and second radiations R1 and R2 are emitted from the first and second radiation sources 6A and 6B, respectively, is 15 fps.

Figure 5:
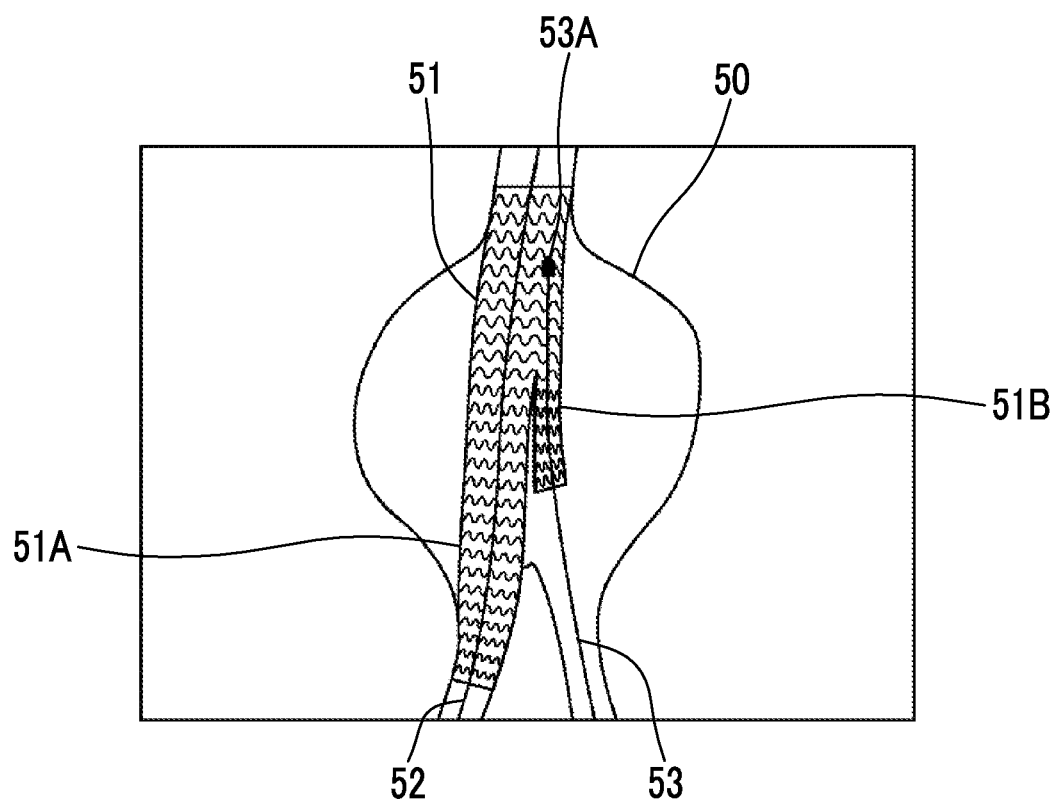
FIG. 5 is a diagram illustrating a radioscopic image displayed in a case in which a catheter treatment is performed.

Here, a medical procedure in a case in which a catheter treatment is performed for the abdominal aneurysm of the subject H using the radiography apparatus 1 according to this embodiment will be described. FIG. 5 is a diagram illustrating a radioscopic image displayed on the user interface 16 in a case in which a catheter treatment is performed. As illustrated in FIG. 5, in a case in which a catheter treatment for the abdominal aneurysm is performed, a bifurcated stent 51 inserted into a guide wire 52 is inserted into the aorta 50 from the artery in one groin and one branch 51A of the stent 51 is expanded by the guide wire 52. Then, an operation is performed which inserts another guide wire 53 into the aorta 50 from the artery in the other groin and passes the guide wire 53 through the other branch 51B of the stent 51 to expand the branch 51B of the stent 51. In this case, in this embodiment, the first radiographic image G1 or the second radiographic image G2 of the abdominal aneurysm of the subject H is displayed as a radioscopic image of the moving image on the user interface 16. The user performs an operation of passing the guide wire 53 through the branch 51B of the stent 51 while viewing the radioscopic image displayed on the user interface 16.

Figure 6:
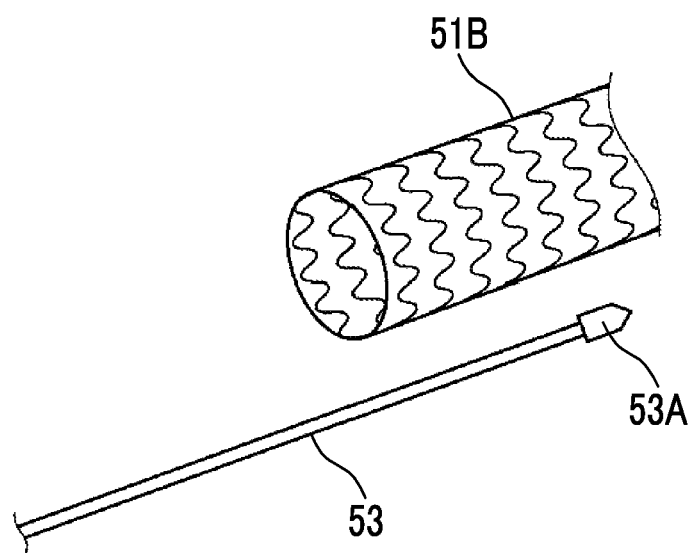
FIG. 6 is a diagram illustrating a state in which there is a difference between the positions of a stent and a guide wire.

Here, the diameter of the branch 51B of the stent 51 is small and the radioscopic image displayed on the user interface 16 is a two-dimensional image. Therefore, it is difficult to know a three-dimensional positional relationship between an end portion of the branch 51B of the stent 51 and a leading end 53A of the guide wire 53. For example, in the radioscopic image illustrated in FIG. 5, the guide wire 53 seems to be inserted into the branch 51B of the stent 51. However, in practice, as illustrated in FIG. 6, there is a possibility that the guide wire 53 will not be inserted into the branch 51B.

Figure 7:
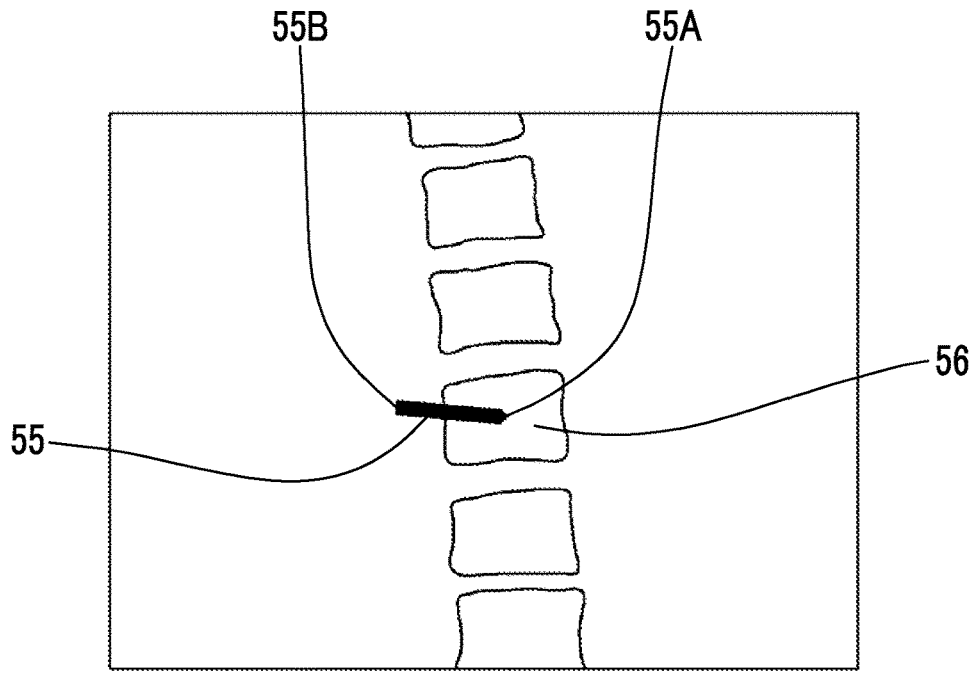
FIG. 7 is a diagram illustrating lumbar spine fusion.

Further, in a case in which lumbar spine fusion is performed, a radiographic image of the front of the subject H is captured, a screw insertion position is determined, a radioscopic image of the side of the subject H illustrated in FIG. 7 is displayed as a moving image, and a screw 55 is inserted into the lumbar spine 56 while a depth and an angle are checked. However, since the radioscopic image is a two-dimensional image, it is difficult to know the insertion position and insertion angle of the screw 55 and erroneous insertion is likely to occur. This embodiment has been made in order to solve these problems.

The feature point detection unit 32 detects at least one common feature point in the subject H from each of the first and second radiographic images G1 and G2 included in the radiographic image set. For example, in the case of the catheter treatment, the leading end 53A of the guide wire 53 included in each of the first and second radiographic images G1 and G2 is detected as the feature point. The guide wire 53 is an insertion structure according to the present disclosure. In the case of the lumbar spine fusion, a leading end 55A and a rear end 55B of the screw 55 included in each of the first and second radiographic images G1 and G2 are detected as the feature points. The screw 55 is the insertion structure according to the present disclosure. In this embodiment, the feature point detection unit 32 has a learned model which has been trained so as to detect the feature points in the first and second radiographic images G1 and G2.

The feature point includes not only one pixel but also a region having a certain area formed by a plurality of pixels. For example, the leading end 53A of the guide wire 53, the leading end 55A of the screw 55, and the rear end 55B of the screw 55 have a certain area and are included in the feature points in this embodiment.

The learned model is a neural network that has been subjected to deep-learning so as to detect the feature points included in the first and second radiographic images G1 and G2. The learned model is generated by training a neural network using a large number of images, in which feature points have been known, as training data. Therefore, in a case in which the first and second radiographic images G1 and G2 are input, the feature point detection unit 32 detects a common feature point from the first and second radiographic images G1 and G2 and outputs the two-dimensional position coordinates of the detected feature point.

The learned model may be, for example, a support vector machine (SVM), a convolutional neural network (CNN), and a recurrent neural network (RNN) in addition to the neural network subjected to deep learning.

In this embodiment, the feature point detection unit 32 detects the feature points using the learned model. However, the invention is not limited thereto. For example, any method, such as a method for detecting the feature points included in the first and second radiographic images G1 and G2 using template matching, may be used as a method for detecting the feature points.

Figure 8:
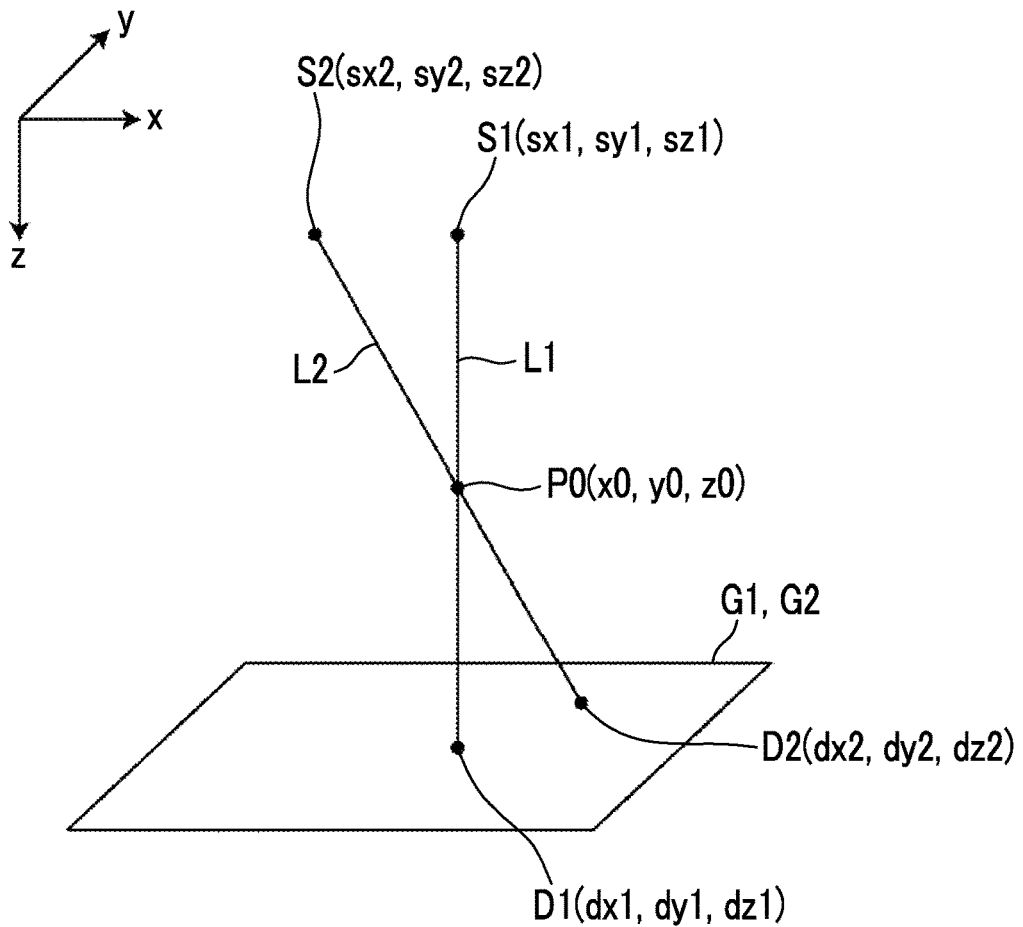
FIG. 8 is a diagram illustrating the derivation of three-dimensional positional information of a feature point.

The second positional information derivation unit 33 derives the three-dimensional positional information of the feature point in the subject H as second positional information, using the positional relationship between the position of the feature point detected from the first and second radiographic images G1 and G2 on the detection surface 5A of the radiation detector 5 and the positions of the first and second radiation sources 6A and 6B. FIG. 8 is a diagram illustrating the derivation of the three-dimensional positional information of the feature point. The second positional information derivation unit 33 acquires the information of a radiation source position S1 (sx1, sy1, sz1) of the first radiation source 6A, a radiation source position S2 (sx2, sy2, sz2) of the second radiation source 6B, a position D1 (dx1, dy1, dz1) of the feature point detected in the first radiographic image G1, and a position D2 (dx2, dy2, dz2) of the feature point detected in the second radiographic image G2 illustrated in FIG. 8.

In a case in which a coordinate system having, as the origin, any position on the C-arm 2 of the radiography apparatus 1 is set, the three-dimensional coordinates (sx1, sy1, sz1) of the radiation source position S1 and the three-dimensional coordinates (sx2, sy2, sz2) of the radiation source position S2 can be derived on the basis of the positional relationship between the origin and the first and second radiation sources 6A and 6B. For example, in this embodiment, a coordinate system having, as the origin, a point that bisects a line connecting the centers of the first and second emission portions 4A and 4B of the radiation emitting unit 4 can be set.

Since the SID is known, it is possible to derive the three-dimensional coordinates of the center position of the detection surface 5A of the radiation detector 5 with respect to the origin. In addition, it is possible to derive the three-dimensional coordinates of the positions D1 and D2 of the feature point from the two-dimensional position coordinates of the feature point in the first and second radiographic images G1 and G2 detected by the feature point detection unit 32, using the three-dimensional coordinates of the center position of the detection surface 5A of the radiation detector 5.

The second positional information derivation unit 33 sets a straight line L1 connecting the radiation source position S1 and the position D1 of the feature point and a straight line L2 connecting the radiation source position S2 and the position D2 of the feature point. Any point P1 on the straight line L1 and any point P2 on the straight line L2 are expressed by the following Expression (1) using the radiation source positions S1 and S2 and the positions D1 and D2 of the feature point. In Expression (1), t and s are parameters.

$$P1 = (1-t) \cdot S1 + t \cdot D1$$

$$P2 = (1-s) \cdot S2 + s \cdot D2 \qquad (1)$$

Ideally, the feature point in the subject H detected in the first and second radiographic images G1 and G2 is located at an intersection point between the point P1 on the straight line L1 and the point P2 on the straight line L2 in a three-dimensional space. Therefore, in this embodiment, the second positional information derivation unit 33 derives the three-dimensional coordinates of a point, at which the distance between the point P1 and the point P2 is the minimum, as second positional information P0(x0, y0, z0) which is the three-dimensional positional information of the feature point detected in the first and second radiographic images G1 and G2, using the following Expression (2):

$$P0 = \min(P1 - P2)^2 \qquad (2).$$

In a case in which the insertion structure is the guide wire 53, the second positional information derivation unit 33 derives the three-dimensional coordinates of the leading end 53A of the guide wire 53 as the second positional information. In a case in which the insertion structure is the screw 55, the second positional information derivation unit 33 derives the three-dimensional coordinates of the leading end 55A and the rear end 55B of the screw 55 as the second positional information.

In a case in which the image acquisition unit 31 acquires a radiographic image set including the first and second radiographic images G1 and G2 at successive time points, the second positional information derivation unit 33 derives the second positional information P0 using the first and second radiographic images G1 and G2 included in the acquired radiographic image set. Therefore, the time point when the second positional information derivation unit 33 derives the second positional information P0 is a time point T4 illustrated in FIG. 4.

Figure 9:
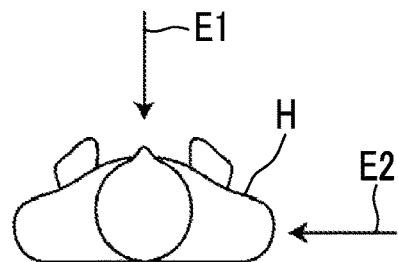
FIG. 9 is a diagram illustrating imaging in two directions.

Next, the first positional information derivation unit 30 will be described. The first positional information derivation unit 30 captures the images of the subject H in two directions and derives the three-dimensional positional information of at least one target point of a target structure, which is a target during a medical procedure, in the subject H as the first positional information. For example, in the case of a catheter treatment for the abdominal aneurysm, first, an operation is performed which expands the branch 51A after the stent 51 is inserted and inserts the guide wire 53 into the branch 51B. Therefore, the first positional information derivation unit 30 derives the three-dimensional coordinates of the center position of an end portion of the branch 51B of the stent 51 as the first positional information. The stent 51 is the target structure according to the present disclosure and the center position of the end portion of the branch 51B of the stent 51 is the target point according to the present disclosure. The target point includes not only one pixel but also a region having a certain area formed by a plurality of pixels. FIG. 9 is a diagram illustrating the capture of the images of the subject H in two directions and FIG. 10 is a diagram illustrating radiographic images acquired by the imaging in two directions.

Figure 10:
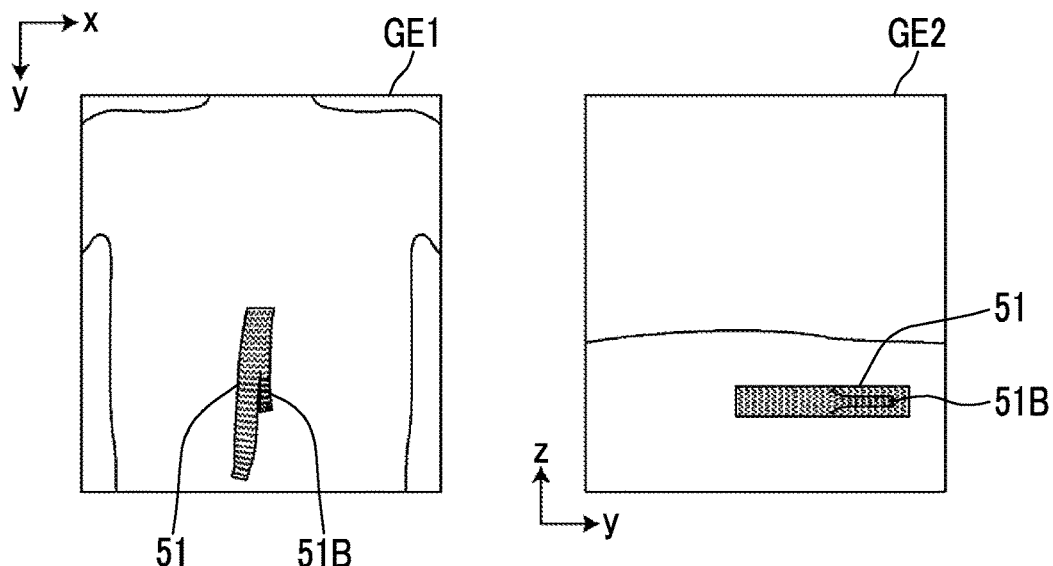
FIG. 10 is a diagram illustrating radiographic images acquired by imaging in two directions.

The C-arm 2 is moved to the state illustrated in FIG. 1 and the imaging control unit 14 irradiates the subject H with radiation in the direction of an arrow E1 illustrated in FIG. 9 to acquire a radiographic image GE1 illustrated in FIG. 10 in response to a command from the user. In addition, the radiation emitting unit 4 is moved to the right side of the subject H in FIG. 1 and the subject H is irradiated with radiation in the direction of an arrow E2 to acquire a radiographic image GE2 illustrated in FIG. 10. The radiographic images GE1 and GE2 include the image of the stent 51. The coordinates of the center positions of the radiographic images GE1 and GE2 are known since they are matched with the coordinates of the center position of the detection surface 5A of the radiation detector 5. Therefore, the first positional information derivation unit 30 derives the three-dimensional coordinates of the center position of the end portion of the branch 51B, into which the guide wire for the stent 51 is to be inserted, in the radiographic images GE1 and GE2 as the first positional information which is the three-dimensional positional information of the target point in the same coordinate system as that in a case in which the feature point is detected.

Here, the coordinate system is not limited to the same coordinate system as that in a case in which the feature point is detected. For example, a coordinate system having the center position of the end portion of the branch 51B of the stent 51 as the origin may be set.

In addition, the first positional information derivation unit 30 may direct the radiography apparatus 1 to perform tomosynthesis imaging to generate a three-dimensional image of a target part of the subject H and may derive the first positional information from the three-dimensional image acquired by the tomosynthesis imaging.

In the tomosynthesis imaging, while the C-arm 2 is being rotated in the direction of the arrow A, one (here, the first radiation source 6A) of the first and second radiation sources 6A and 6B emits radiation at a plurality of radiation source positions to capture the images of the subject H, thereby acquiring a plurality of projection images. Then, the first positional information derivation unit 30 reconstructs the plurality of projection images using a back projection method, such as a simple back projection method or a filtered back projection method, to generate tomographic images in a plurality of tomographic planes of the subject H. Then, a three-dimensional image formed by the plurality of tomographic images is generated.

The first positional information derivation unit 30 performs coordinate transform such that the coordinate system of the three-dimensional image is matched with the coordinate system of the feature point and derives the three-dimensional coordinates of the center position of the end portion of the branch 51B of the stent 51 as the first positional information. In this case, a coordinate system having the center position of the end portion of the branch 51B of the stent 51 as the origin may be set.

In addition, the first positional information derivation unit 30 may derive the first positional information from a three-dimensional image which has been acquired in advance by, for example, a CT apparatus and an MRI apparatus. In this case, similarly to the three-dimensional image acquired by the tomosynthesis imaging, the first positional information derivation unit 30 may perform coordinate transform such that the coordinate system of the three-dimensional image which has been acquired in advance is matched with the coordinate system of the feature point and may derive the three-dimensional coordinates of the center position of the end portion of the branch 51B of the stent 51 as the first positional information. In this case, a coordinate system having the center position of the end portion of the branch 51B of the stent 51 as the origin may be set.

Figure 11:
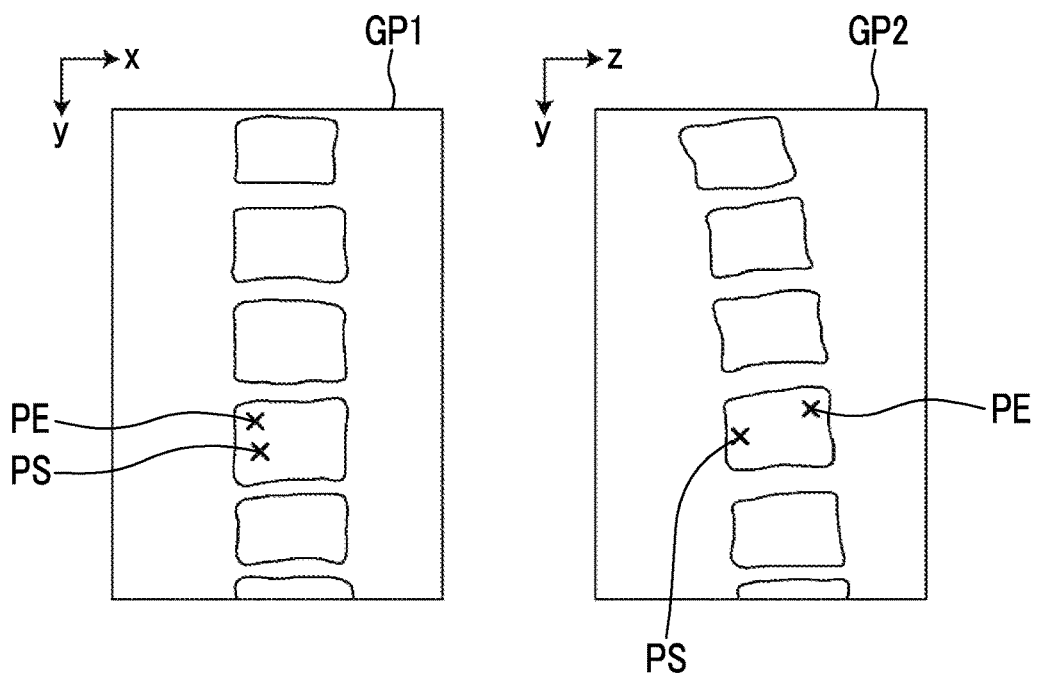
FIG. 11 is a diagram illustrating projection images in two directions generated from a three-dimensional image.

In contrast, in a case in which lumbar spine fusion is performed, the first positional information derivation unit 30 derives, as the first positional information, the three-dimensional coordinates of an insertion position and an arrival position in the lumbar spine which have been specified in advance in the three-dimensional image of the subject H acquired by the CT apparatus or the MRI apparatus before a medical procedure. The lumbar spine is the target structure according to the present disclosure and the insertion position and the arrival position are the target points according to the present disclosure. In this case, the first positional information derivation unit 30 generates projection images GP1 and GP2 obtained by projecting the three-dimensional image in the direction of the arrow E1 and the direction of the arrow E2 illustrated in FIG. 9, respectively. FIG. 11 is a diagram illustrating the projection images in two directions. As illustrated in FIG. 11, the projection image GP1 is a front view of the lumbar spine of the subject H and the projection image GP2 is a side view of the lumbar spine of the subject H. Here, the insertion position and the arrival position of the screw 55 are predetermined and set on the three-dimensional image by an examination before a medical procedure. Therefore, an insertion position PS and an arrival position PE are specified in the projection images GP1 and GP2.

Figure 12:
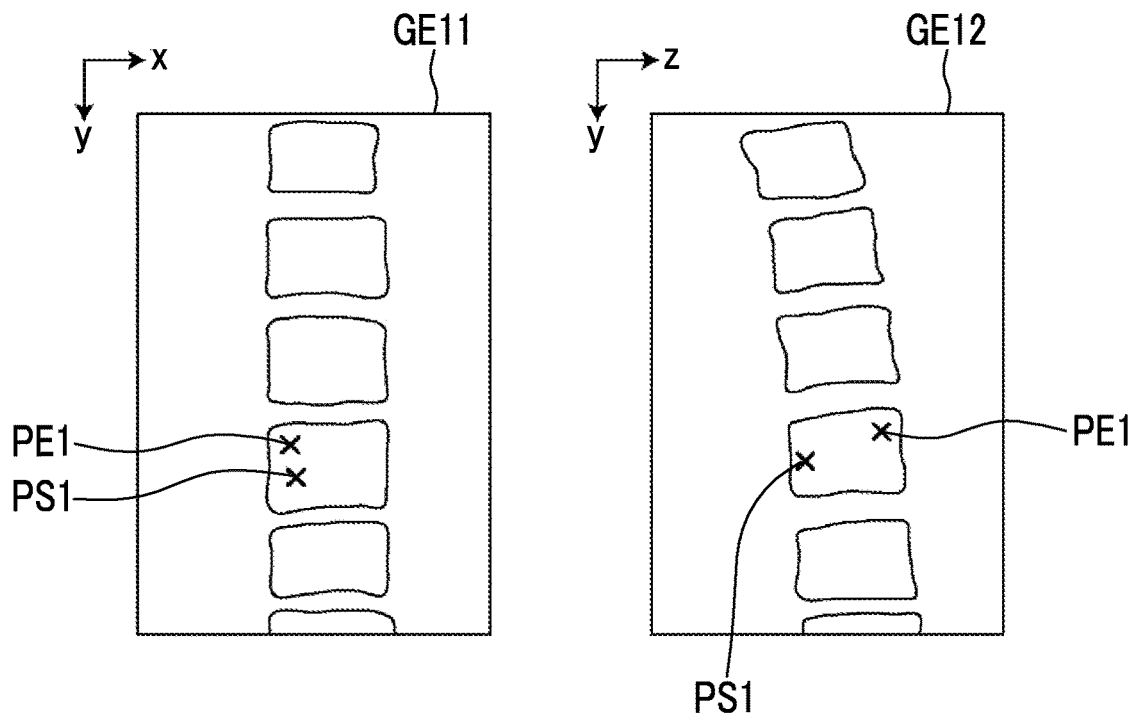
FIG. 12 is a diagram illustrating radiographic images acquired by imaging in two directions.

In addition, the first positional information derivation unit 30 captures the images of the subject H in the two directions illustrated in FIG. 9 and acquires radiographic images GE11 and GE12 illustrated in FIG. 12. Then, the first positional information derivation unit 30 matches the coordinate system of the radiographic images GE11 and GE12 with the coordinate system of the projection images GP1 and GP2 and specifies an insertion position PS1 and an arrival position PE1 in the radiographic images GE11 and GE12. In this case, it is preferable that the coordinate systems to be matched with each other have the insertion position PS in the projection images GP1 and GP2 as the origin. However, the invention is not limited thereto. The coordinate system of the radiographic images GE11 and GE12 may be matched with a coordinate system having any point on the projection images GP1 and GP2 as the origin or the coordinate system of the projection images GP1 and GP2 may be matched with the coordinate system of the radiographic images GE11 and GE12.

The display control unit 34 displays a positional information screen indicating the positional relationship between the target point and the feature point on the user interface 16.

Figure 13:
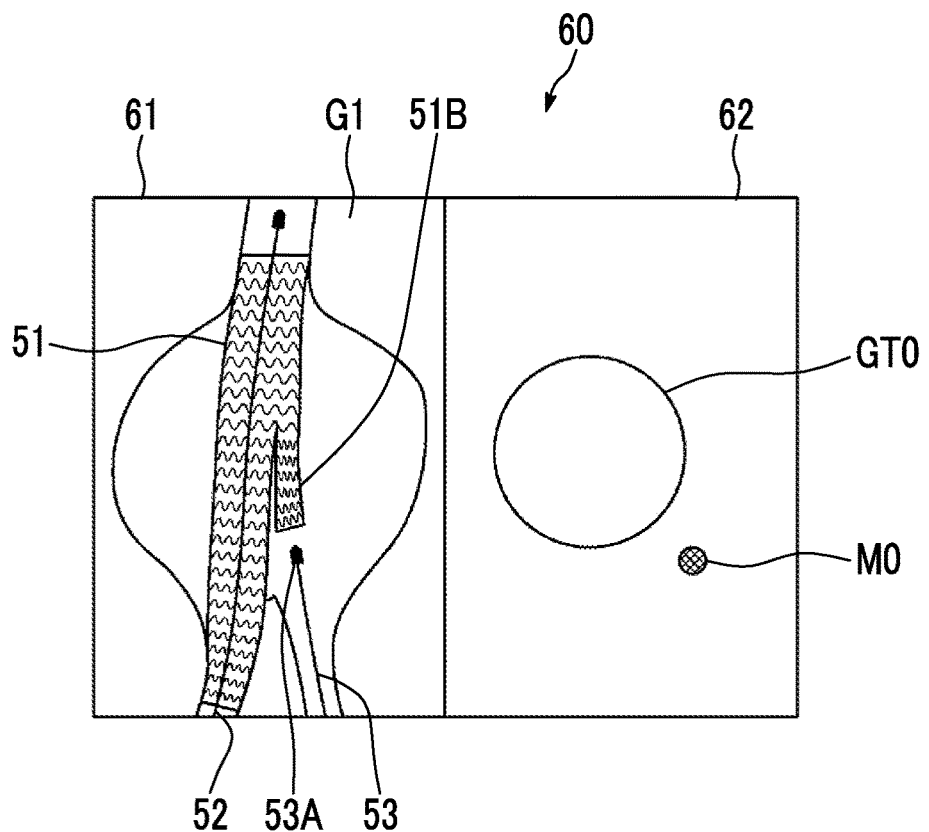
FIG. 13 is a diagram illustrating a positional information screen in the case of a catheter treatment.

FIG. 13 is a diagram illustrating a positional information screen in a case in which a catheter treatment is performed. As illustrated in FIG. 13, a positional information screen 60 has a radioscopic image display region 61 and a positional relationship display region 62. The first radiographic image G1 which is a portion of the radiographic image set is sequentially displayed as a radioscopic image in the display region 61. Therefore, the radioscopic images are displayed as a moving image in the display region 61. In addition, the second radiographic image G2 may be sequentially displayed as the radioscopic image in the display region 61.

Here, the first positional information derivation unit 30 derives the three-dimensional coordinates of the center position of the branch 51B of the stent 51 as the first positional information and the second positional information derivation unit 33 derives the three-dimensional coordinates of the leading end 53A of the guide wire 53 as the second positional information P0. In addition, the diameter of the branch 51B of the stent 51 is known. Therefore, the display control unit 34 generates a stent image GT0 schematically indicating the shape of the branch 51B of the stent 51 and displays the stent image GT0 in the positional relationship display region 62. The stent image GT0 is an image as the end portion of the branch 51B of the stent 51 is viewed from the direction of the central axis. Further, the display control unit 34 displays a mark M0 indicating the position of the leading end 53A of the guide wire 53 in the display region 62. In this case, the display control unit 34 matches the positional relationship between the mark M0 and the stent image GT0 with the positional relationship between the leading end 53A of the guide wire 53 and the center position of the branch 51B of the stent 51 on the basis of the first positional information and the second positional information P0. Here, the position of the leading end 53A of the guide wire 53 is acquired in three-dimensional coordinates. Therefore, the mark M0 indicates the position of the leading end 53A of the guide wire 53 in the image in which the branch 51B of the stent 51 is viewed from the direction of the central axis.

The user performs an operation of inserting the guide wire 53 into the body of the subject H while viewing the positional information screen 60 such that the mark M0 is located in a circle indicating the end portion of the branch 51B in the stent image GT0. Here, the positional relationship between the stent image GT0 and the mark M0 illustrated in FIG. 13 indicates that the leading end 53A of the guide wire 53 is separated from the end portion of the branch 51B of the stent 51. While viewing the positional information screen 60, the user can adjust the position of the guide wire 53 inserted into the subject H such that the mark M0 is located in the stent image GT0. Therefore, it is possible to reduce errors in the insertion of the guide wire 53 into the stent 51 as illustrated in FIG. 6.

The notification unit 35 notifies that the feature point has reached the target point. Specifically, the notification unit 35 notifies that the guide wire 53 has reached the center position of the branch 51B of the stent 51 and has been inserted into the branch 51B through the user interface 16. The notification may be performed by text display or sound. Further, both display and sound may be used for the notification.

Further, the sound may be changed according to the distance between the leading end 53A of the guide wire 53 and the center position of the branch 51B. For example, a beep sound may be intermittently output as the sound and the interval between the beep sounds may become shorter as the leading end 53A of the guide wire 53 becomes closer to the center position of the branch 51B. In addition, the sound may be changed in a case in which the leading end 53A of the guide wire 53 is inserted into the branch 51B.

In a case in which the leading end 53A of the guide wire 53 passes through the end portion of the branch 51B without being inserted into the branch 51B or the distance between the leading end 53A of the guide wire 53 and the center position of the branch 51B is equal to or greater than a predetermined threshold value, the notification unit 35 may issue a warning indicating the fact through the user interface 16.

Figure 14:
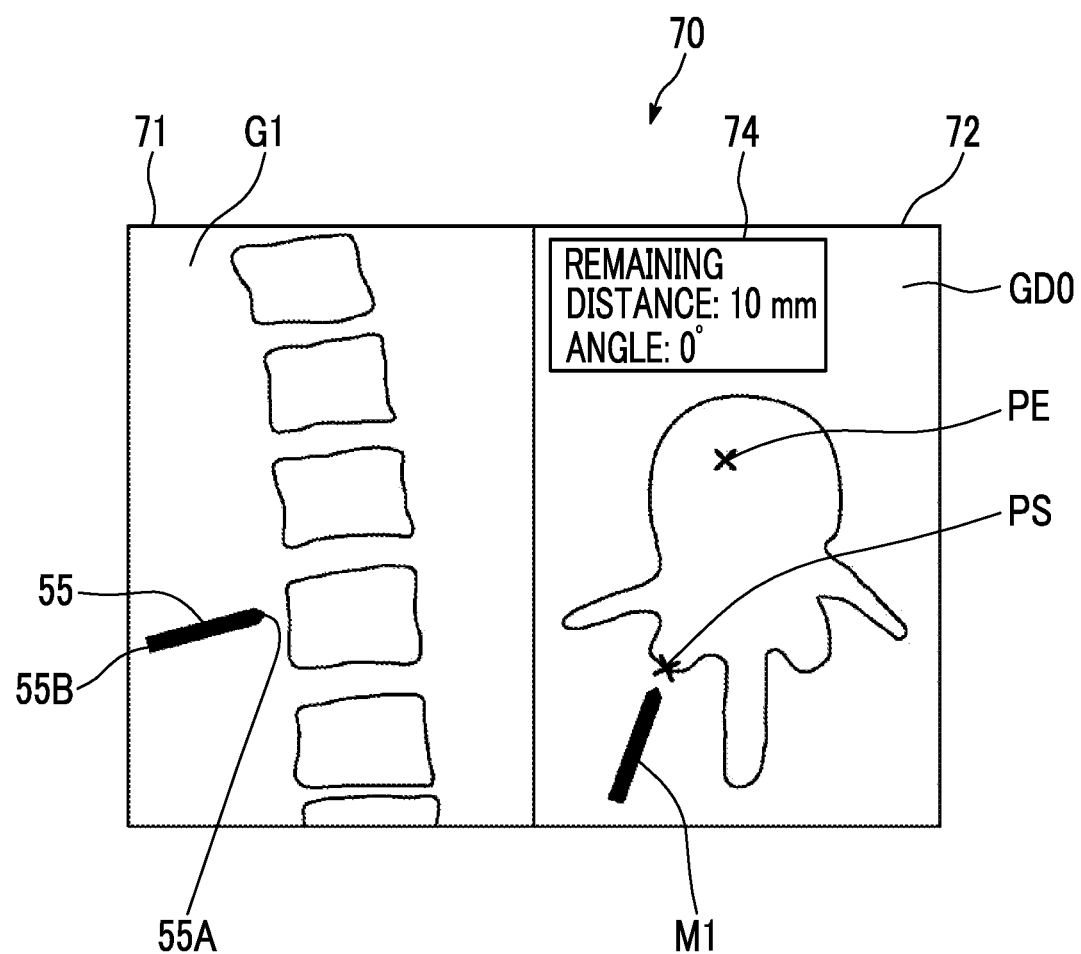
FIG. 14 is a diagram illustrating a positional information screen in the case of lumbar spine fusion.

FIG. 14 illustrates a positional information screen in a case in which lumbar spine fusion is performed. As illustrated in FIG. 14, a positional information screen 70 has a radioscopic image display region 71 and a positional relationship display region 72. The first radiographic image G1 which is a portion of the radiographic image set and is obtained by capturing the image of the lumbar spine from the side is sequentially displayed in the display region 71. Therefore, the radioscopic images are displayed as a moving image in the display region 71. The first radiographic image G1 includes an image of the screw 55. Further, the second radiographic image G2 may be sequentially displayed as a radioscopic image in the display region 71.

Here, the first positional information derivation unit 30 derives the three-dimensional coordinates of the insertion position PS and the arrival position PE of the screw 55 in the lumbar spine as the first positional information. The second positional information derivation unit 33 derives the three-dimensional coordinates of the leading end 55A and the rear end 55B of the screw 55 as the second positional information P0. Therefore, the display control unit 34 generates a tomographic image GD0 of the lumbar spine into which the screw 55 is inserted, using the three-dimensional image of the subject H which has been acquired in advance, and displays the generated tomographic image GD0 in the positional relationship display region 72. The tomographic image GD0 of the lumbar spine displayed in the display region 72 indicates an axial cross section.

The display control unit 34 displays a mark M1 obtained by projecting the screw 55 derived by the second positional information derivation unit 33 onto the tomographic plane of the tomographic image GD0 in the positional relationship display region 72. In this case, the display control unit 34 matches the positional relationship between a leading end and a rear end of the mark M1 and the insertion position PS and the arrival position PE on the tomographic image GD0 with the positional relationship between the leading end 55A and the rear end 55B of the screw 55 and the insertion position PS and the arrival position PE on the three-dimensional image on the basis of the first positional information and the second positional information P0. Further, the display control unit 34 displays the remaining distance from the leading end 55A of the screw 55 derived by the second positional information derivation unit 33 to the insertion position PS derived by the first positional information derivation unit 30 in an information display region 74 until the screw 55 reaches the insertion position PS. The notification unit 35 may display the information display region 74. In this embodiment, since the coordinate system having the insertion position PS as the origin is also set for the radiographic images G1 and G2, it is possible to derive the distance from the current position of the leading end 55A of the screw 55 from the origin as the remaining distance from the leading end 55A of the screw 55 to the insertion position PS.

Further, the display control unit 34 derives an angle (referred to as a first angle) of the axis of the screw 55 with respect to the axial cross section from the positions of the leading end 55A and the rear end 55B of the screw 55 derived by the second positional information derivation unit 33. In addition, an angle (referred to as a second angle) at which the screw 55 is to be inserted is derived from the insertion position PS and the arrival position PE derived by the first positional information derivation unit 30. Then, the difference of the first angle from the second angle is derived and the derived angle is displayed in the information display region 74. In FIG. 14, a remaining distance of 10 mm and an angle of 0 degrees are displayed. The angle of 0 degrees indicates that the angle at which the screw 55 is inserted is matched with the angle formed by the insertion position PS and the arrival position PE. After the screw 55 is inserted into the lumbar spine from the insertion position PS, the remaining distance from the leading end 55A of the screw 55 to the arrival position PE may be displayed in the information display region 74.

The notification unit 35 may issue a warning in a case in which the leading end 55A of the screw 55 is at a position that is separated from the insertion position PS by a predetermined threshold value or more. Further, in a case in which the angle of the screw 55 is greater than a predetermined threshold value (for example, 10 degrees), the display control unit 34 may issue a warning.

The user can insert the screw 55 into the body of the subject H such that the screw 55 is inserted into the lumbar spine from the insertion position PS while viewing the display of the tomographic image GD0, the mark M1, and the information display region 74. In addition, the user can insert the screw 55 into the lumbar spine of the subject H such that the inserted screw 55 correctly reaches the arrival position PE.

Even in the case of lumbar spine fusion, the notification unit 35 may notify that the leading end 55A of the screw 55 has reached the insertion position PS and the leading end 55A of the screw 55 has reached the arrival position PE through the user interface 16. In addition, the notification may be performed in a case in which the angle of the screw 55 is matched with the angle at which the screw 55 is to be inserted. The notification may be performed by text display or sound. Further, both display and sound may be used.

Further, the sound may be changed according to the distance between the leading end 55A of the screw 55 and the insertion position PS and the arrival position PE. For example, a beep sound may be intermittently output as the sound and the interval between the beep sounds may become shorter as the leading end 55A of the screw 55 becomes closer to the insertion position PS and the arrival position PE. In addition, the sound may be changed in a case in which the leading end 55A of the screw 55 reaches the insertion position PS and the arrival position PE.

Figure 15:
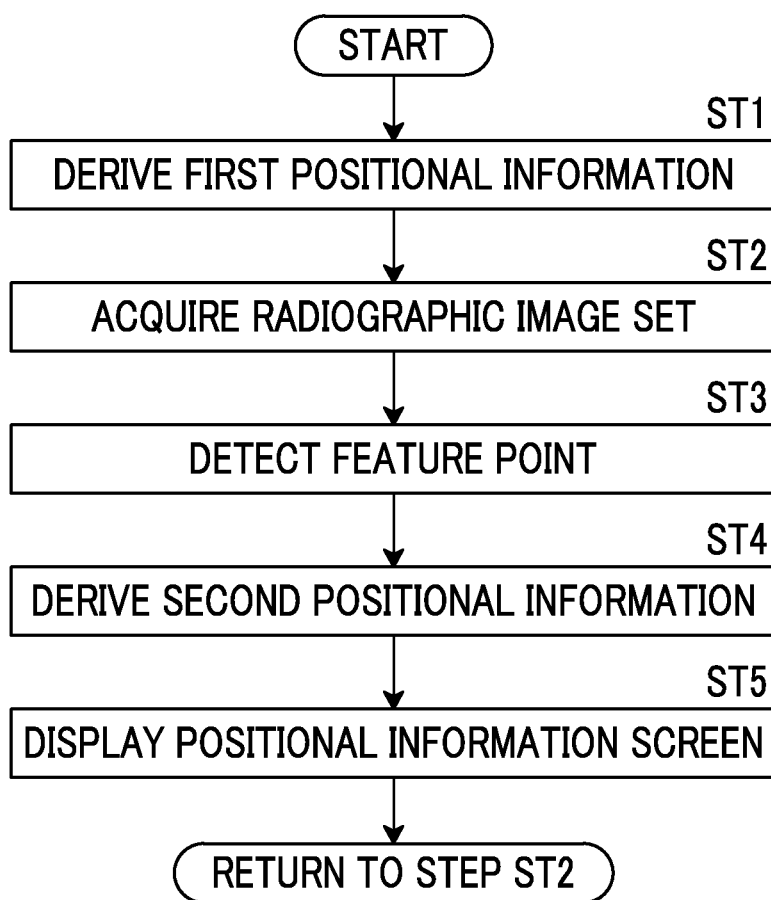
FIG. 15 is a flowchart illustrating a process performed in this embodiment.

Next, a process performed in this embodiment will be described. FIG. 15 is a flowchart illustrating the process performed in this embodiment. First, the first positional information derivation unit 30 derives the three-dimensional positional information of at least one target point of a target structure in the subject H as the first positional information (Step ST1).

Then, the user inputs an imaging start command through the user interface 16 to start the capture of the image of the subject H and the image acquisition unit 31 acquires a set of the first radiographic image G1 and the second radiographic image G2 (the acquisition of a radiographic image set; Step ST2). In a case in which the set of the first radiographic image G1 and the second radiographic image G2 is acquired, the feature point detection unit 32 detects at least one common feature point from the first and second radiographic images G1 and G2 (Step ST3). Then, the second positional information derivation unit 33 derives the three-dimensional positional information of at least one feature point in the subject H as the second positional information, using the positional relationship between the position of at least one feature point detected from each of the first and second radiographic images G1 and G2 on the detection surface 5A of the radiation detector 5 and the positions of the first and second radiation sources 6A and 6B (Step ST4).

The display control unit 34 displays a positional information screen on the user interface 16 (Step ST5). The process returns to Step ST2. The process from Step ST2 to Step ST5 is repeatedly performed until a process end command is issued.

As such, in this embodiment, the first positional information of at least one target point of the target structure in the subject H is derived and the three-dimensional second positional information of at least one feature point on the insertion structure inserted to the target structure in the subject H is derived. Then, a positional information screen indicating the positional relationship between the target point and the feature point is displayed on the user interface 16. Therefore, it is possible to display the positional relationship between the target point and the feature point with a smaller amount of calculation than that in a case in which the positions of the images are aligned. As a result, according to this embodiment, it is possible to understand the positional relationship between the target structure and the insertion structure in the subject H in real time.

In the above-described embodiment, the first radiographic image G1 and the second radiographic image G2 are alternately acquired. However, the invention is not limited thereto. As illustrated in FIG. 16, one second radiographic image G2 may be acquired for every several frames of the first radiographic images G1. In FIG. 16, the second radiographic image G2 is acquired once while four frames of the first radiographic images G1 are acquired. In this case, the derivation of the positional information is performed once while four frames of the first radiographic images G1 are acquired.

In the above-described embodiment, in a case in which a catheter treatment is performed, the first positional information derivation unit 30 derives the three-dimensional coordinates of the center position of the branch 51B of the stent 51 as the first positional information from the radiographic images GE1 and GE2 or the three-dimensional image of the subject H. However, the invention is not limited thereto. The feature point detection unit 32 may detect the center position of the branch 51B of the stent 51 as the target point from the first and second radiographic images G1 and G2 and the first positional information derivation unit 30 may perform the same process as the second positional information derivation unit 33 to derive the three-dimensional coordinates of the center position of the branch 51B as the first positional information on the basis of the target point detected by the feature point detection unit 32.

In the above-described embodiment, the first positional information derivation unit 30 derives the three-dimensional positional information of the target point of the target structure as the first positional information from, for example, the radiographic images GE1 and GE2 and the projection images GP1 and GP2 generated from and the three-dimensional image of the subject H. However, the invention is not limited thereto. For example, the radiographic images GE1 and GE2 may be displayed on the user interface 16 and the first positional information may be derived in response to a command to set a target point on the displayed images which is received from the user.

In the above-described embodiment, radiation is not particularly limited and rays other than X-rays, such as α-rays or γ-rays, may be applied.

In the above-described embodiment, in a case in which a catheter treatment and lumbar spine fusion are performed, the positional information display device and the radiography apparatus according to the present disclosure are applied. However, the invention is not limited thereto. The present disclosure may be applied to any medical procedure using a radioscopic image.

In the above-described embodiment, the first and second radiation sources 6A and 6B are arranged in the y-axis direction illustrated in FIG. 1 in the radiation emitting unit 4. However, the first and second radiation sources 6A and 6B may be arranged in the x-axis direction.

In the above-described embodiment, the radiation emitting unit 4 includes the two radiation sources 6A and 6B. However, the invention is not limited thereto. The radiation emitting unit 4 may include three or more radiation sources. In this case, the positional information may be derived using a plurality of radiographic images acquired by irradiating the subject H with radiation emitted from three or more radiation sources. Specifically, the positional information may be derived using a combination of two radiographic images generated by radiation emitted from two radiation sources among three or more radiation sources.

In the above-described embodiment, for example, the following various processors can be used as the hardware structure of processing units performing various processes, such as the first positional information derivation unit 30, the image acquisition unit 31, the feature point detection unit 32, the second positional information derivation unit 33, the display control unit 34, and the notification unit 35. The various processors include a CPU which is a general-purpose processor executing software (program) to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

What is claimed is:

1. A positional information display device comprising:
at least one processor configured to:
derive three-dimensional positional information of at least one target point of a target structure in a subject as first positional information, according to two-dimensional positional information of the at least one target point, based on a plurality of source image distances, wherein each of the plurality of source image distances is a distance between a detection surface of a radiation detector and each of a plurality of radiation sources, and the radiation detector comprises a flat panel detector comprising the detection surface,
wherein the plurality of radiation sources comprises a first radiation source and a second radiation source, the first radiation source and the second radiation source are arranged side by side in a first direction, and a first radiation and a second radiation in a second direction perpendicular to the first direction are emitted respectively from the first radiation source and the second radiation source;
derive three-dimensional positional information of at least one feature point on an insertion structure inserted to the target structure in the subject as second positional information, according to two-dimensional positional information of the at least one feature point, based on the plurality of source image distances;
display a positional information screen indicating a positional relationship between the at least one target point and the at least one feature point on a display;
acquire a radiographic image set including a plurality of radiographic images, which have been generated by alternately irradiating the subject with radiation emitted from the plurality of radiation sources provided at different positions and alternately detecting the radiation transmitted through the subject using the radiation detector, at a predetermined time interval, wherein the different positions comprises a first radiation source position of the first radiation source and a second radiation source position of the second radiation source;
detect the at least one feature point on the insertion structure inserted to the target structure in the subject from each of the plurality of radiographic images included in the radiographic image set; and
derive the second positional information using a positional relationship between a position of the at least one feature point detected from each of the plurality of radiographic images on the detection surface of the radiation detector and positions of the plurality of radiation sources.

2. The positional information display device according to claim 1, wherein the at least one processor further is configured to display the positional information screen including a radiographic image display region in which some of the plurality of radiographic images are displayed and a positional relationship display region in which the positional relationship is displayed on the display.

3. The positional information display device according to claim 1, wherein the at least one processor further is configured to provide a display signal or a sound signal that the at least one feature point has reached the at least one target point.

4. The positional information display device according to claim 3, wherein the at least one processor further is configured to issue a warning in a case in which the at least one feature point deviates from the at least one target point by a predetermined distance or a predetermined angle.

5. The positional information display device according to claim 1,
wherein the insertion structure is a surgical instrument that is inserted into the subject.

6. The positional information display device according to claim 1,
wherein the target structure is a stent that is inserted into a blood vessel of the subject,
the at least one target point is a center position of an end portion of the stent,
the insertion structure is a guide wire for expanding the stent, and
the at least one feature point is a leading end of the guide wire.

7. The positional information display device according to claim 1,
wherein the target structure is a lumbar spine of the subject,
the at least one target point is at least one of an insertion position or an arrival position of a screw that is inserted into the lumbar spine,
the insertion structure is the screw, and
the at least one feature point is at least one of a leading end or a rear end of the screw.

8. A radiography apparatus comprising:
a plurality of radiation sources that are provided at a predetermined interval;
a positional information display device according to claim 1;
a radiation detector configured to be arranged towards the plurality of radiation sources, the radiation detector being configured to detect radiation, which has been emitted from each of the plurality of radiation sources and transmitted through a subject to generate a radiographic image of the subject; and
at least one processor configured to generate a radiographic image set including a plurality of radiographic images at a predetermined time interval by controlling a time point when each of the plurality of radiation sources emits the radiation and a time point when the radiation detector detects the radiation transmitted through the subject such that the plurality of radiation sources alternately irradiate the subject with the radiation and the radiation detector alternately detects the radiation transmitted through the subject.

9. The radiography apparatus according to claim 8,
wherein the plurality of radiation sources comprises two radiation sources.

10. The radiography apparatus according to claim 9,
wherein the at least one processor is further configured to:
direct one of the two radiation sources to sequentially emit radiation at a first time interval, direct the other radiation source to sequentially emit radiation at a second time interval equal to or longer than the first time interval, and control the radiation detector so as to detect the radiation at all time points when the two radiation sources emit the radiation, and
acquire, as the radiographic image set, two radiographic images generated by detecting two temporally adjacent radiation using the radiation detector, the two temporally adjacent radiation having been emitted from the two radiation sources.

11. A positional information display method comprising:
  deriving three-dimensional positional information of at least one target point of a target structure in a subject as first positional information, according to two-dimensional positional information of the at least one target point, based on a plurality of source image distances, wherein each of the plurality of source image distances is a distance between a detection surface of a radiation detector and each of a plurality of radiation sources, and the radiation detector comprises a flat panel detector comprising the detection surface,
  wherein the plurality of radiation sources comprises a first radiation source and a second radiation source, the first radiation source and the second radiation are arranged side by side in a first direction, and a first radiation and a second radiation in a second direction perpendicular to the first direction are emitted respectively from the first radiation source and the second radiation source;
  deriving three-dimensional positional information of at least one feature point on an insertion structure inserted to the target structure in the subject as second positional information, according to two-dimensional positional information of the at least one feature point, based on the plurality of source image distances;
  displaying a positional information screen indicating a positional relationship between the at least one target point and the at least one feature point on a display;
  acquiring a radiographic image set including a plurality of radiographic images, which have been generated by alternately irradiating the subject with radiation emitted from the plurality of radiation sources provided at different positions and alternately detecting the radiation transmitted through the subject using the radiation detector, at a predetermined time interval, wherein the different positions comprises a first radiation source position of the first radiation source and a second radiation source position of the second radiation source;
  detecting the at least one feature point on the insertion structure inserted to the target structure in the subject from each of the plurality of radiographic images included in the radiographic image set; and
  deriving the second positional information using a positional relationship between a position of the at least one feature point detected from each of the plurality of radiographic images on the detection surface of the radiation detector and positions of the plurality of radiation sources.

12. A non-transitory computer-readable storage medium that stores a positional information display program that causes a computer to perform:
  a step of deriving three-dimensional positional information of at least one target point of a target structure in a subject as first positional information, according to two-dimensional positional information of the at least one target point, based on a plurality of source image distances, wherein each of the plurality of source image distances is a distance between a detection surface of a radiation detector and each of a plurality of radiation sources, and the radiation detector comprises a flat panel detector comprising the detection surface,
  wherein the plurality of radiation sources comprises a first radiation source and a second radiation source, the first radiation source and the second radiation source are arranged side by side in a first direction, and a first radiation and a second radiation in a second direction perpendicular to the first direction are emitted respectively from the first radiation source and the second radiation source;
  a step of deriving three-dimensional positional information of at least one feature point on an insertion structure inserted to the target structure in the subject as second positional information, according to two-dimensional positional information of the at least one feature point, based on the plurality of source image distances;
  a step of displaying a positional information screen indicating a positional relationship between the at least one target point and the at least one feature point on a display;
  a step of acquiring a radiographic image set including a plurality of radiographic images, which have been generated by alternately irradiating the subject with radiation emitted from the plurality of radiation sources provided at different positions and alternately detecting the radiation transmitted through the subject using the radiation detector, at a predetermined time interval, wherein the different positions comprises a first radiation source position of the first radiation source and a second radiation source position of the second radiation source;
  a step of detecting the at least one feature point on the insertion structure inserted to the target structure in the subject from each of the plurality of radiographic images included in the radiographic image set; and,
  a step of deriving the second positional information using a positional relationship between a position of the at least one feature point detected from each of the plurality of radiographic images on the detection surface of the radiation detector and positions of the plurality of radiation sources.

13. A positional information display device comprising:
  at least one processor configured to:
    derive three-dimensional positional information of at least one target point of a target structure in a subject as first positional information;
    acquire a radiographic image set including a plurality of radiographic images, which have been generated by alternately irradiating the subject with radiation emitted from a plurality of radiation sources provided at different positions and alternately detecting the radiation transmitted through the subject using a radiation detector, at a predetermined time interval;
    detect at least one feature point on an insertion structure inserted to the target structure in the subject from each of the plurality of radiographic images included in the radiographic image set by using a learned model, which has been trained so as to detect the at least one feature point from the plurality of radiographic images;
    derive, as second positional information, three-dimensional positional information of the at least one feature point using a positional relationship between a position of the at least one feature point detected from each of the plurality of radiographic images on a detection surface of the radiation detector and positions of the plurality of radiation sources; and
    display a positional information screen indicating a positional relationship between the at least one target point and the at least one feature point on a display.

14. The positional information display device according to claim 13, wherein the processor further configured to:
  display the positional information screen including a radiographic image display region in which some of the plurality of radiographic images are displayed and a positional relationship display region in which the positional relationship is displayed on the display.

15. The positional information display device according to claim 13, wherein the processor further configured to:
    notify that the at least one feature point has reached the at least one target point.

16. The positional information display device according to claim 15, wherein the processor further configured to:
    issue a warning in a case in which the at least one feature point deviates from the at least one target point by a predetermined distance or a predetermined angle.

17. The positional information display device according to claim 13, wherein the insertion structure is a surgical instrument that is inserted into the subject.

18. The positional information display device according to claim 13,
    wherein the target structure is a stent that is inserted into a blood vessel of the subject,
    the at least one target point is a center position of an end portion of the stent,
    the insertion structure is a guide wire for expanding the stent, and
    the at least one feature point is a leading end of the guide wire.

19. The positional information display device according to claim 13,
    wherein the target structure is a lumbar spine of the subject,
    the at least one target point is at least one of an insertion position or an arrival position of a screw that is inserted into the lumbar spine,
    the insertion structure is the screw, and
    the at least one feature point is at least one of a leading end or a rear end of the screw.

20. A radiography apparatus comprising:
    a plurality of radiation sources that are provided at a predetermined interval;
    a positional information display device according to claim 14; and
    a radiation detector configured to be arranged towards the plurality of radiation sources, the radiation detector being configured to detect radiation, which has been emitted from each of the plurality of radiation sources and transmitted through a subject to generate a radiographic image of the subject, and
    at least one processor configured to generate a radiographic image set including a plurality of radiographic images at a predetermined time interval by controlling a time point when each of the plurality of radiation sources emits the radiation and a time point when the radiation detector detects the radiation transmitted through the subject such that the plurality of radiation sources alternately irradiate the subject with the radiation and the radiation detector alternately detects the radiation transmitted through the subject.

21. The radiography apparatus according to claim 20, wherein the plurality of the radiation sources comprises two radiation sources.

22. The radiography apparatus according to claim 21, wherein the at least one processor is further configured to:
    direct one of the two radiation sources to sequentially emit radiation at a first time interval, direct the other radiation source to sequentially emit radiation at a second time interval equal to or longer than the first time interval, and control the radiation detector so as to detect the radiation at all time points when the two radiation sources emit the radiation, and
    acquire, as the radiographic image set, two radiographic images generated by detecting two temporally adjacent radiation using the radiation detector, the two temporally adjacent radiation having been emitted from the two radiation sources.

\* \* \* \* \*